(12) United States Patent
Kurd et al.

(10) Patent No.: US 10,842,483 B2
(45) Date of Patent: Nov. 24, 2020

(54) DEVICES AND METHODS FOR SUTURE PLACEMENT

(71) Applicant: Dura Tap LLC, Wayne, PA (US)

(72) Inventors: Mark F. Kurd, Wayne, PA (US); David Greg Anderson, Villanova, PA (US); Jaime F. Sarabia, Mableton, GA (US); Eric Buehlmann, Duxbury, MA (US); Jay P. Tapper, Wayne, PA (US); Jens Johnson, Austin, TX (US); Ann R. Lee, Philadelphia, PA (US); Catherine Margaret Unruh, Reading, PA (US)

(73) Assignee: DURASTAT LLC, Wayne, PA (US)

( * ) Notice: Subject to any disclaimer, the term of this patent is extended or adjusted under 35 U.S.C. 154(b) by 204 days.

(21) Appl. No.: 16/073,819

(22) PCT Filed: Nov. 22, 2016

(86) PCT No.: PCT/US2016/063308
§ 371 (c)(1),
(2) Date: Jul. 30, 2018

(87) PCT Pub. No.: WO2017/136027
PCT Pub. Date: Aug. 10, 2017

(65) Prior Publication Data
US 2019/0029669 A1  Jan. 31, 2019

Related U.S. Application Data

(60) Provisional application No. 62/291,602, filed on Feb. 5, 2016.

(51) Int. Cl.
*A61B 17/04* (2006.01)
*A61B 17/062* (2006.01)
(Continued)

(52) U.S. Cl.
CPC ...... *A61B 17/0625* (2013.01); *A61B 17/0469* (2013.01); *A61B 17/062* (2013.01);
(Continued)

(58) Field of Classification Search
CPC ............ A61B 17/0625; A61B 17/0469; A61B 17/0482; A61B 17/062; A61B 17/0483;
(Continued)

(56) References Cited

U.S. PATENT DOCUMENTS

| 1,822,330 A | 1/1930 | Ainslie |
| 5,364,408 A | 11/1994 | Gordon |

(Continued)

FOREIGN PATENT DOCUMENTS

| EP | 0140557 | 5/1985 |
| JP | 2011194162 | 10/2011 |

OTHER PUBLICATIONS

Supplemental EP Search Report filed in EP 16 88 9643 dated Oct. 23, 2019.

(Continued)

*Primary Examiner* — Melaine R Tyson
(74) *Attorney, Agent, or Firm* — Rankin, Hill & Clark, LLP

(57) ABSTRACT

A suturing device includes an elongate body, an actuator, a needle holder and a knot pusher. The elongate body includes a proximal end portion and a distal end portion. The actuator interacts with the elongate body and is operable between a first operating position and a second operating position. The needle holder extends away from the distal end portion or is provided as part of the distal end portion of the elongate body, and includes a distal end section having a distal-most tip. The needle holder defines a needle passage and a distal opening adjacent the distal-most tip. The knot pusher con- (Continued)

nects with and extends away from at least one of the elongate body and the needle holder.

18 Claims, 15 Drawing Sheets

(51) Int. Cl.
    *A61B 17/06*     (2006.01)
    *A61B 17/00*     (2006.01)

(52) U.S. Cl.
    CPC .. *A61B 17/06004* (2013.01); *A61B 17/06066* (2013.01); *A61B 17/06109* (2013.01); *A61B 17/06114* (2013.01); *A61B 2017/00738* (2013.01); *A61B 2017/00867* (2013.01); *A61B 2017/00946* (2013.01); *A61B 2017/0472* (2013.01); *A61B 2017/0474* (2013.01); *A61B 2017/0608* (2013.01); *A61B 2017/06052* (2013.01); *A61B 2017/06057* (2013.01)

(58) Field of Classification Search
    CPC ...... A61B 2017/047; A61B 2017/0474; A61B 2017/0475; A61B 2017/0477
    See application file for complete search history.

(56) References Cited

U.S. PATENT DOCUMENTS

| | | |
|---|---|---|
| 5,387,221 A | 2/1995 | Bisgaard |
| 5,713,910 A | 2/1998 | Gordon |
| 5,741,276 A | 4/1998 | Poloyko et al. |
| 5,741,279 A | 4/1998 | Gordon |
| 5,817,107 A | 10/1998 | Schaller |
| 6,719,764 B1 | 4/2004 | Gellman et al. |
| 6,916,314 B2 | 7/2005 | Schneider et al. |
| 6,936,054 B2 | 8/2005 | Chu |
| 7,112,208 B2 | 9/2006 | Morris |
| 7,122,039 B2 | 10/2006 | Chu |
| 7,582,096 B2 | 9/2009 | Gellman et al. |
| 7,803,167 B2 | 9/2010 | Nobles et al. |
| 7,815,654 B2 | 10/2010 | Chu |
| 7,967,832 B2 | 6/2011 | Chu |
| 7,981,125 B1 * | 7/2011 | Colvin ............... A61B 17/0467 606/148 |
| 8,361,089 B2 | 1/2013 | Chu |
| 8,496,676 B2 | 7/2013 | Nobles et al. |
| 8,518,058 B2 | 8/2013 | Gellman et al. |
| 8,702,729 B2 | 4/2014 | Chu |
| 8,764,771 B2 | 7/2014 | Chu |
| 8,906,041 B2 | 12/2014 | Chu |
| 9,504,465 B2 | 11/2016 | Chu |
| 9,549,728 B2 | 1/2017 | Chu |
| 9,572,570 B2 | 2/2017 | Gellman et al. |
| 9,814,459 B2 | 11/2017 | Gellman et al. |
| 2003/0233104 A1 * | 12/2003 | Gellman ........... A61B 17/0469 606/139 |
| 2006/0206119 A1 | 9/2006 | Chu |
| 2006/0293699 A1 | 12/2006 | Robertson |
| 2007/0213745 A1 * | 9/2007 | Takemoto ........ A61B 17/12013 606/144 |
| 2009/0312772 A1 | 12/2009 | Chu |
| 2010/0057109 A1 | 3/2010 | Clerc |

OTHER PUBLICATIONS

International Search Report filed in PCT/US/63308 dated Feb. 3, 2017.

* cited by examiner

DEVICES AND METHODS FOR SUTURE PLACEMENT

This application claims priority to U.S. Provisional Application Ser. No. 62/291,602 filed on Feb. 5, 2016, the entirety of which is expressly incorporated by reference.

BACKGROUND

The present disclosure relates generally to surgery and the placement of sutures, and more particularly, to devices and methods for the suture repair of tissue, for example, tears of the dura mater that occur during spinal surgery.

Tears of the dura mater (durotomy) are a relatively common occurrence during spinal surgery. Incidences of durotomy can vary by procedure and can be an additional challenge during surgical repairs such as, for example, lumbar surgeries or the like. Moreover, it is desirable to form a substantially watertight closure of the dura mater to inhibit or preclude, for example, cerebrospinal fluid (CSF) leaks that can otherwise lead to patient complications.

Surgical closure techniques using sutures is one approach to dural repair. In some instances, however, these techniques can be difficult to execute due to anatomic constraints, obstruction of visualization by CSF or blood, and the proximity to nerve rootlets. In some instances, these challenges can be further complicated when using minimally invasive techniques such as, for example, a tubular retractor. In some such instances, surgeons may choose not repair the durotomy or they may attempt to repair the durotomy using traditional suturing tools. Such tools and devices can be limited and, in some instances, lack maneuverability to avoid obstructions and/or to enable adequate passage of the needle and suture through the tissue. As a result, surgical repairs of the dura mater are often time consuming and expensive.

SUMMARY

In view of the foregoing, a suturing device is provided including an elongate body, an actuator, a needle holder and a knot pusher. The elongate body includes a proximal end portion and a distal end portion. The actuator interacts with the elongate body and is operable between a first operating position and a second operating position. The needle holder extends away from the distal end portion or is provided as part of the distal end portion of the elongate body, and includes a distal end section having a distal-most tip. The needle holder defines a needle passage and a distal opening adjacent the distal-most tip. The knot pusher connects with and extends away from at least one of the elongate body and the needle holder.

DETAILED DESCRIPTION

Figure 1:
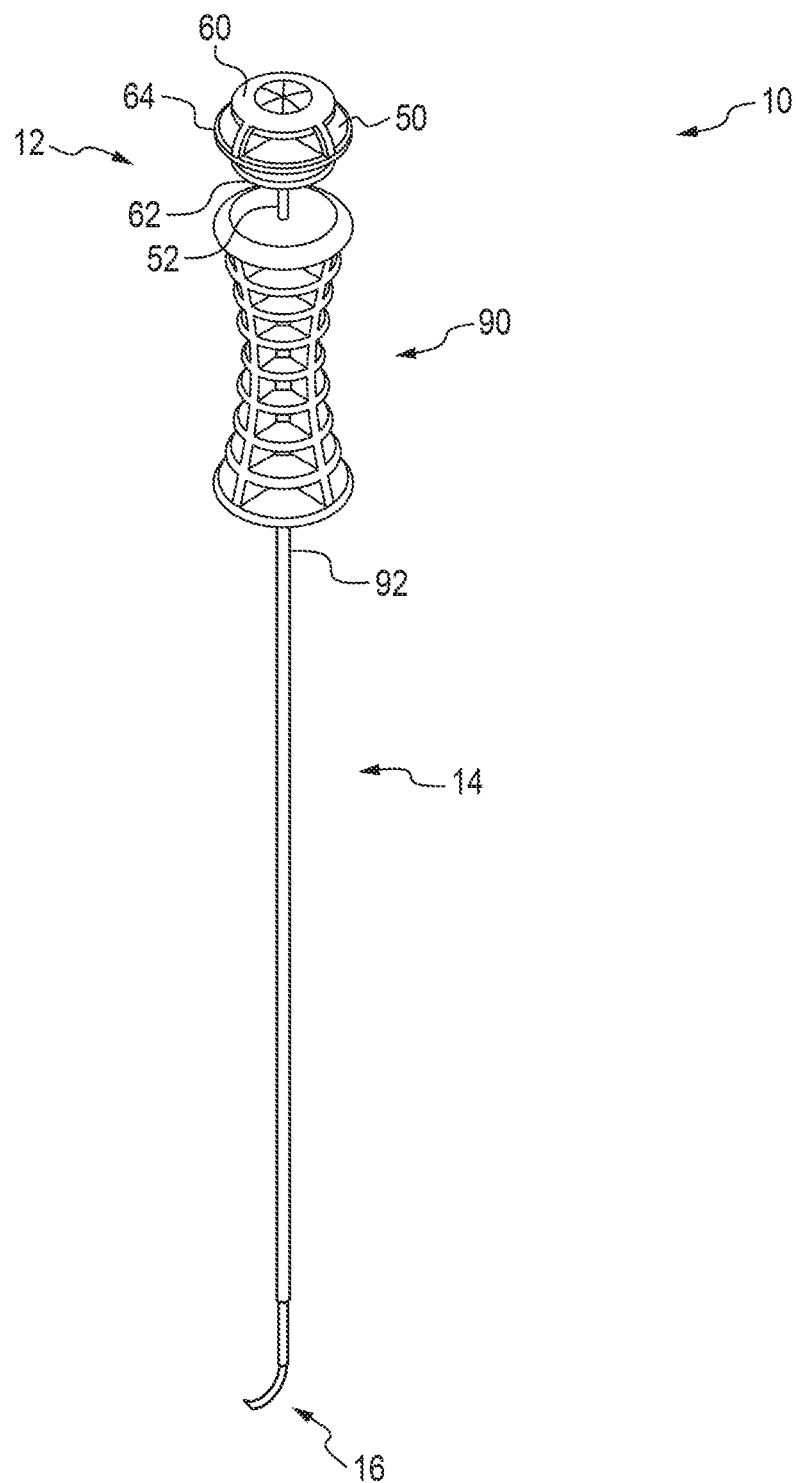
FIG. 1 is a perspective view of a suturing device.
Figure 2:
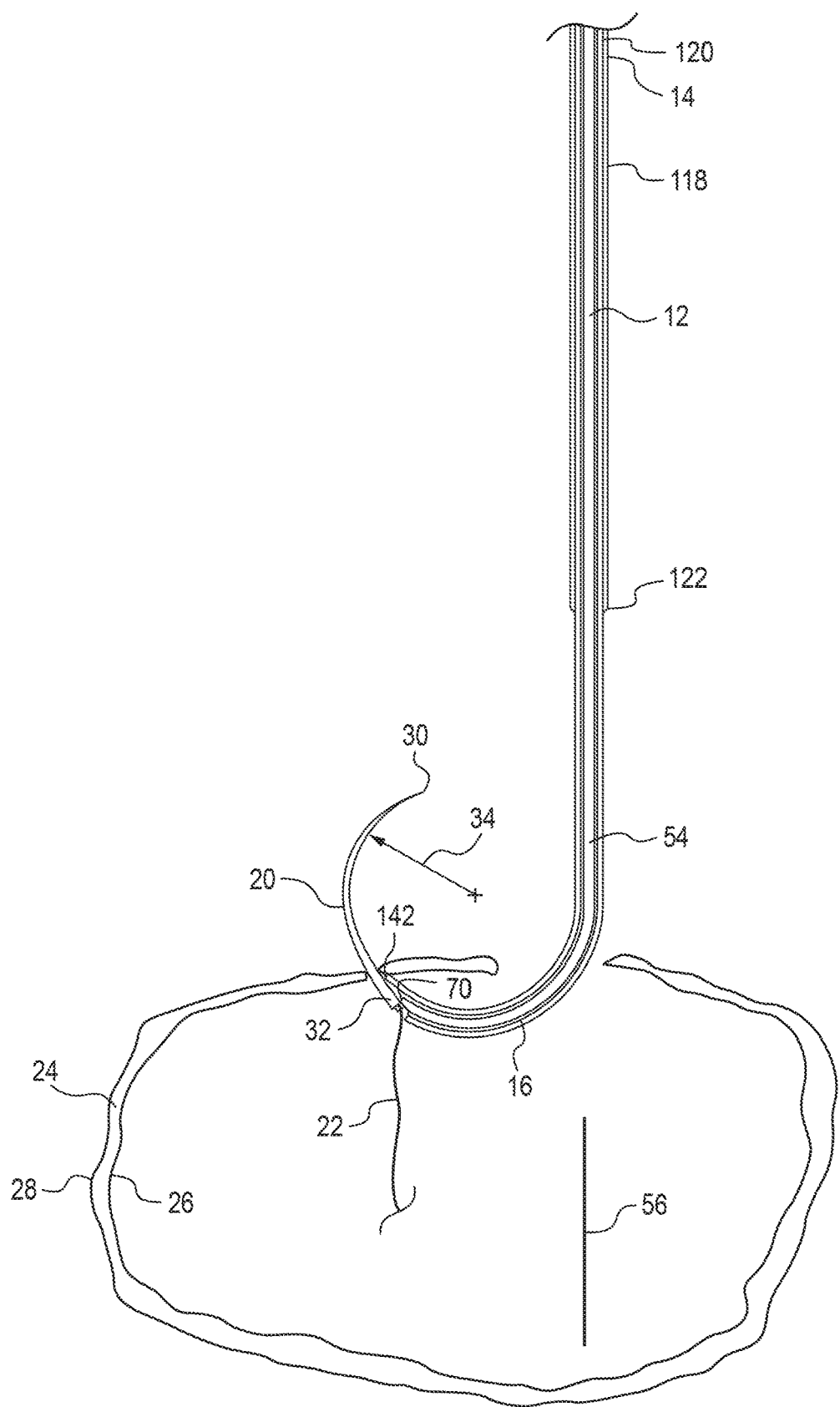
FIG. 2 is a cross-sectional view of a lower portion of the suturing device of FIG. 1 and a schematic depiction of a tissue tear.

FIG. 1 depicts an example of a suturing device 10 that is useful to suture tears in dura mater, which may occur during spinal surgery procedures; however, the suturing device 10 can be used in other types of surgical procedures. The suturing device 10 generally includes an actuator 12, an elongate body 14, and a needle holder 16. The suturing device 10 is particularly useful during a minimally invasive surgical procedure that is performed through a tubular retractor or other small surgical portal to accurately locate a needle 20 and a suture 22, which are shown in FIG. 2, with respect to target tissue 24 to be sutured. The target tissue 24 shown in FIG. 2 is part of a dural sac having a tear. Again, the suturing device 10 may be useful in other surgical procedures.

Figure 3A:
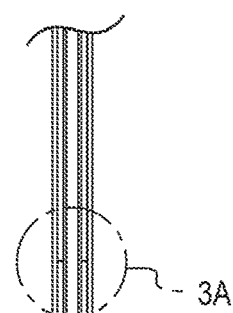
FIG. 3A is an enlarged view of the circled portion in FIG. 3.
Figure 3A:
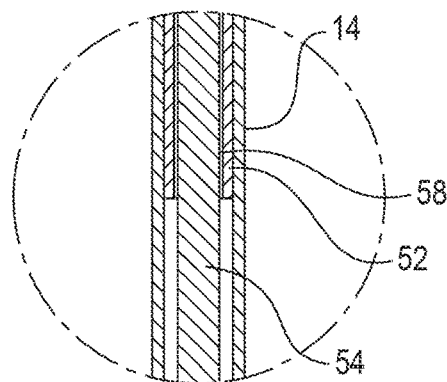
Figure 3:
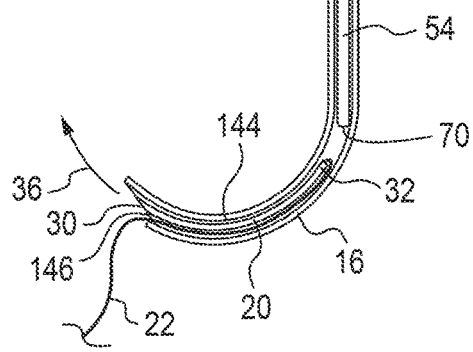
FIG. 3 is another cross-sectional view of the lower portion of the suturing device of FIG. 1.

With reference to FIG. 2, the needle 20 in the illustrated embodiment is a curved needle having a first end 30, which is pointed, and a second end 32, which is opposite to the first end 30. The needle 20 can be similar to commercially available curved needles made from known materials. The needle 20 can be formed having a curved needle radius 34. The needle 20 could also be formed from a malleable, or flexible, material such that the needle 20 could follow a curve when positioned within the needle holder 16, which is curved in FIG. 2, and then later straighten after exiting the needle holder 16. The needle 20 can take other configurations, such as straight. Also, the needle 20 could be formed as part of the suture 22, e.g., the needle 20 could be a rigid end of the suture 22 that is configured so as to be suitable to pass through animal tissue. Actuation of the actuator 12 moves the needle 20 in an advance direction 36 (FIG. 3) with respect to the needle holder 16. The needle 20 moves from a retracted position, which is shown in FIG. 3, to a released condition, which is shown in FIG. 2, in which the needle 20 is released from the needle holder 16. When in the released condition, the surgeon can grasp the needle 20, for example with forceps, and pull the needle 20 and the suture 22.

With reference back to FIG. 2, the suture 22 connects with the needle 20 and extends from the second end 32 of the needle 20. The suture 22 can be swaged to the second end 32 of the needle 20. The suture 22 can also connect with the needle 20 in other conventional manners. The suture 22 can be acquired from known suture manufacturers. The average diameter of the suture 22 can be very close to the outer diameter of the second end 32 of the needle 20, for example, the average diameter of the suture 22 can be between 90% and 110% of the outer diameter of the second end 32 of the needle 20.

Figure 4:
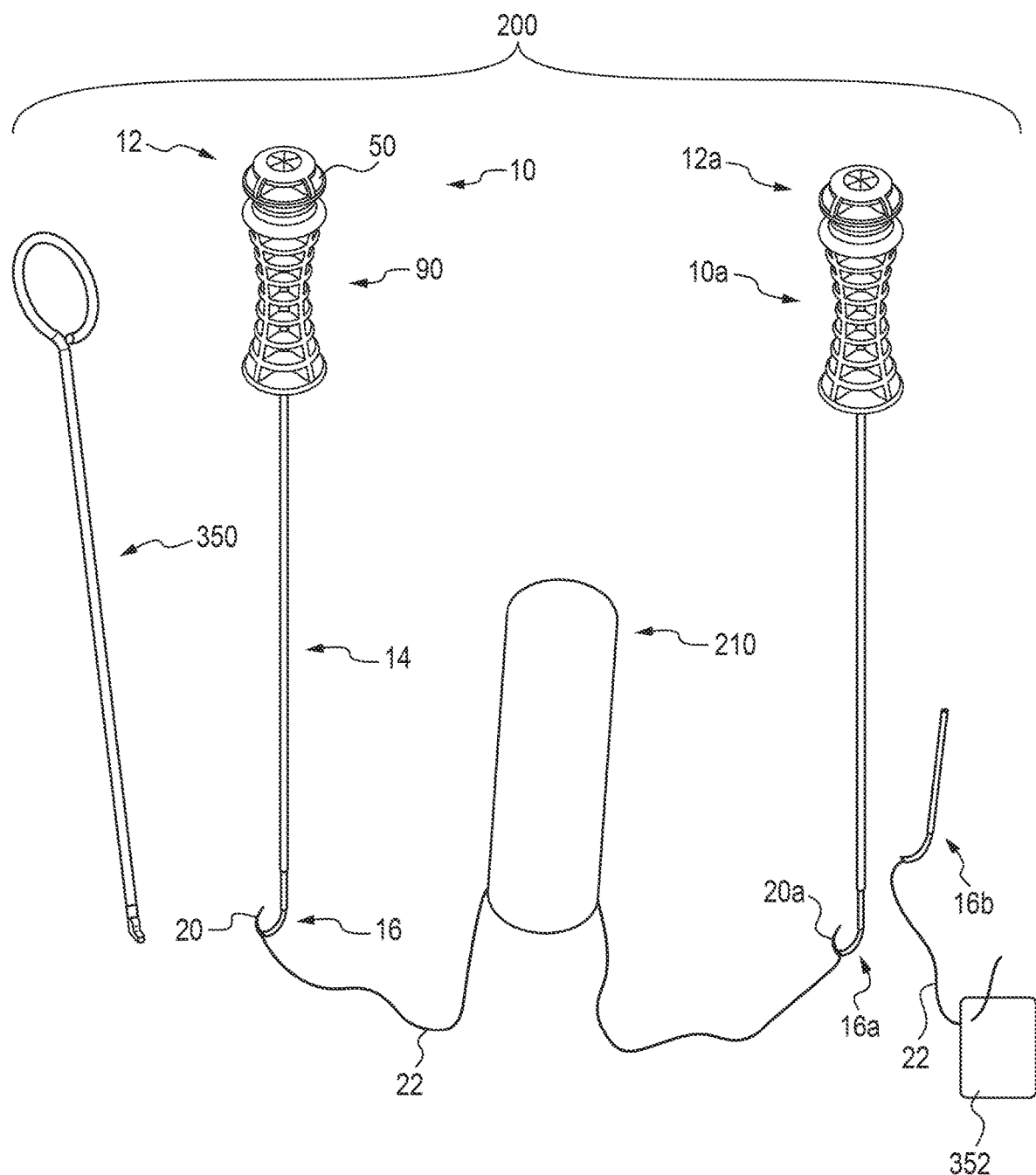
FIG. 4 is a perspective view of a suturing kit including two suturing devices, a suture holding structure and a knot pusher.

The actuator 12 is operable between a first operating position and a second operating position. As seen when comparing FIG. 1 to FIG. 4, the actuator 12 in the illustrated embodiment is moveable between a first operating position, which is shown in FIG. 1, and a second operating position, which is shown in FIG. 4. Movement of the actuator 12 from the first operating position toward the second operating position moves the needle 20 in the advance direction 36 (FIG. 3) with respect to the needle holder 16 thus moving the needle 20 toward the released condition, which is shown in FIG. 2, in which the needle 20 is released from the needle holder 16.

With reference back to FIG. 1, in the illustrated embodiment the actuator 12 includes a button 50, a tube 52, which could also be a rod, and a wire 54 (FIG. 2). In the illustrated embodiment, the button 50 connects with the tube 52, which is connected with the wire 54. Alternatively, the button 50 could connect with the wire 54 without the tube 52. Also, the button 50 could connect with a rod having no elongate passage, and the rod can connect with the wire 54. In the illustrated embodiment, the actuator 12 includes a flexible section, which in the illustrated embodiment is made up of the wire 54, which can be made from nitinol. The flexible section is configured to bend within the needle holder 16 when the actuator 12 is moved from the first operating position toward the second operating position.

The tube 52 (or rod) is received within the elongate body 14 and moves with respect to the elongate body 14 when the actuator 12 moves between the first operating position and the second operating position. In the illustrated embodiment, the tube 52 moves along a longitudinal axis 56 (FIG. 2). The longitudinal axis 56 in the illustrated embodiment is a straight line; however, the longitudinal axis could be a curved line, for example if the elongate body 14 is curved. The tube 52 includes an elongate passage 58, which receives the wire 54 in the illustrated embodiment. Alternatively, the wire 54 could extend from a distal end of a rod, which would connect with the button 50, in lieu of providing the tube 52. The tube 52 is made from a rigid material, such as a rigid plastic or metal, and is more rigid than the wire 54.

With reference back to FIG. 1, the button 50 includes an operator contact surface 60 that is configured to be depressed by a surgeon's finger or thumb to move the actuator 12 from the first operating position toward the second operating position. The button 50 also includes a handle contact surface 62 spaced from the operator contact surface 60 along the longitudinal axis 56. The button 50 also includes an outer surface 64, which follows a surface of revolution about the longitudinal axis 56 and spans between the operator contact surface 60 and the handle contact surface 62, which allows for the surgeon to easily manipulate the suturing device 10 and rotate the suturing device 10 about the longitudinal axis 56. The button 50 connects with the tube 52 (or the rod) and the wire 54 such that movement of the button 50 along the longitudinal axis 56 results in movement of the tube 52 (or rod) and the wire 54 along the longitudinal axis 56.

Figure 5:
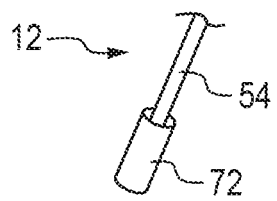
FIGS. 5-7 are perspective views of variations of a lower portion of an actuator of the suturing device of FIG. 1.
Figure 6:
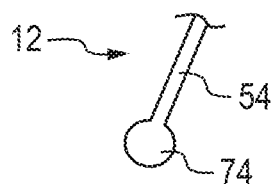
Figure 7:
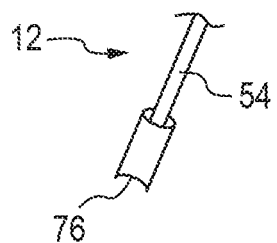

With reference to FIG. 2, a distal end 70 of the actuator 12, which in the illustrated embodiment is located at a distal end of the wire 54, contacts the second end 32 of the needle 20 as the actuator 12 is moved from the first operating position (shown in FIGS. 1 and 3) toward the second operating position (shown in FIGS. 2 and 4) to move the needle 20 in the advance direction 36. With reference to FIG. 5, which shows a lower portion of the actuator 12, the actuator 12 could include a distal tube 72, which could be made from plastic, at a distal portion. As illustrated, the distal tube 72 connects with the wire 54. An outer diameter of the distal tube 72 could be nearly equal to an inner diameter of the elongate body 14 and/or the needle holder 16, while being small enough so that the distal tube 72 is freely moveable within the elongate body 14 and the needle holder 16. An alternative arrangement is shown in FIG. 6, which also shows a distal portion of the actuator 12 where the actuator 12 includes a spherical distal tip 74. As illustrated, the spherical distal tip 74 can be provided on the wire 54. The outer diameter of the spherical distal tip 74 can be nearly equal to the inner diameter of the elongate body 14 and/or the needle holder 16. FIG. 7 also depicts a distal portion of the actuator 12 where the actuator 12 includes a pocket 76 at a distal end. The pocket 76 is configured to receive the second end 32 of the needle 20. The pocket 76 can also be configured to receive the suture 22. The pocket 76 could be formed from a resilient material that clamps onto the second end 32 of the needle 20 while the needle 20 is being advanced through the needle holder 16 in the advance direction 36.

Other types of actuators can be employed to move the needle 20 in the advance direction 36. For example, air pressure through a pneumatic mechanism could be used to move the needle 20 from the retracted position shown in FIG. 3 to the released condition shown in FIG. 2. Other types of mechanical actuators could also be used to move the needle 20. For example, rollers that contact the needle 20 could be driven by a motor to move the needle 20 from the retracted position toward the released condition. Moreover, the needle 20 can be deployed using a robot where the suturing device 10 connects with an end effector of a robot, and the actuator and the suturing device 10 can be configured to connect with the end effector. As such, the actuator 12 including the button 50, the tube 52 and the wire 54 is not the only actuator contemplated to move the needle 20 from the retracted position toward the released condition.

With reference back to FIG. 1, the suturing device 10 also includes a handle 90 connected with the elongate body 14. The handle 90 connects with a proximal end portion 92 of the elongate body 14 and is fixed to the elongate body 14 such that movement of the handle 90, e.g., rotational or translational movement, results in the same movement of the elongate body 14.

Figure 8:
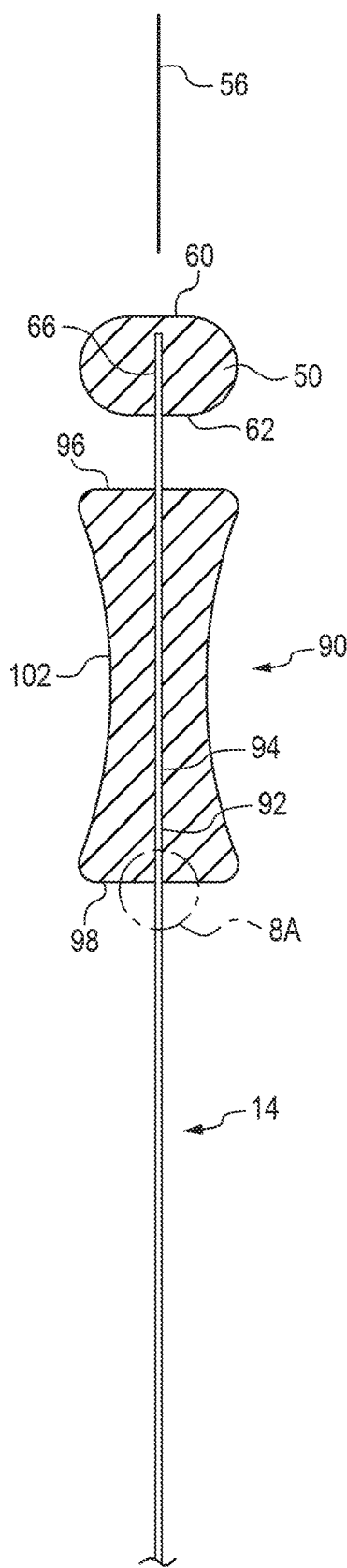
FIG. 8 is a cross-sectional view of an upper portion of the suturing device of FIG. 1.
Figure 8A:
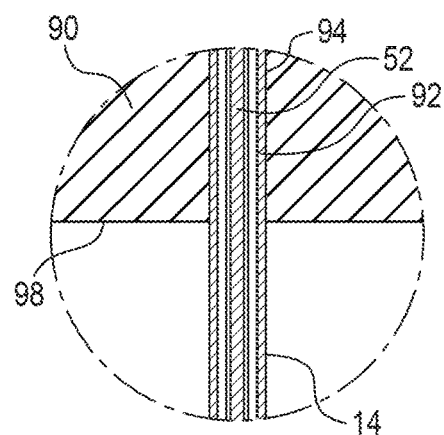
FIG. 8A is an enlarged view of the circled portion in FIG. 8.

With reference to FIGS. 8 and 8A, the handle 90 includes an elongate bore 94 in which the proximal end portion 92 of the elongate body 14 is received. The elongate bore 94 extends from a proximal end surface 96 to a distal end surface 98 and is aligned with the longitudinal axis 56. The handle 90 also defines an outer side surface 102 extending between the proximal end surface 96 and the distal end surface 98. The outer side surface 102 follows a surface of revolution about the longitudinal axis 56. In the illustrated embodiment, the outer side surface 102 is a hyperboloid. An outer diameter of the handle 90 adjacent both the proximal end surface 96 and the distal end surface 98 is less than an outer diameter of the handle 90 equidistant between the proximal end surface 96 and the distal end surface 98. This provides a recessed contour that allows the surgeon to easily grip the handle 90 to maneuver the suturing device 10.

Figure 9:
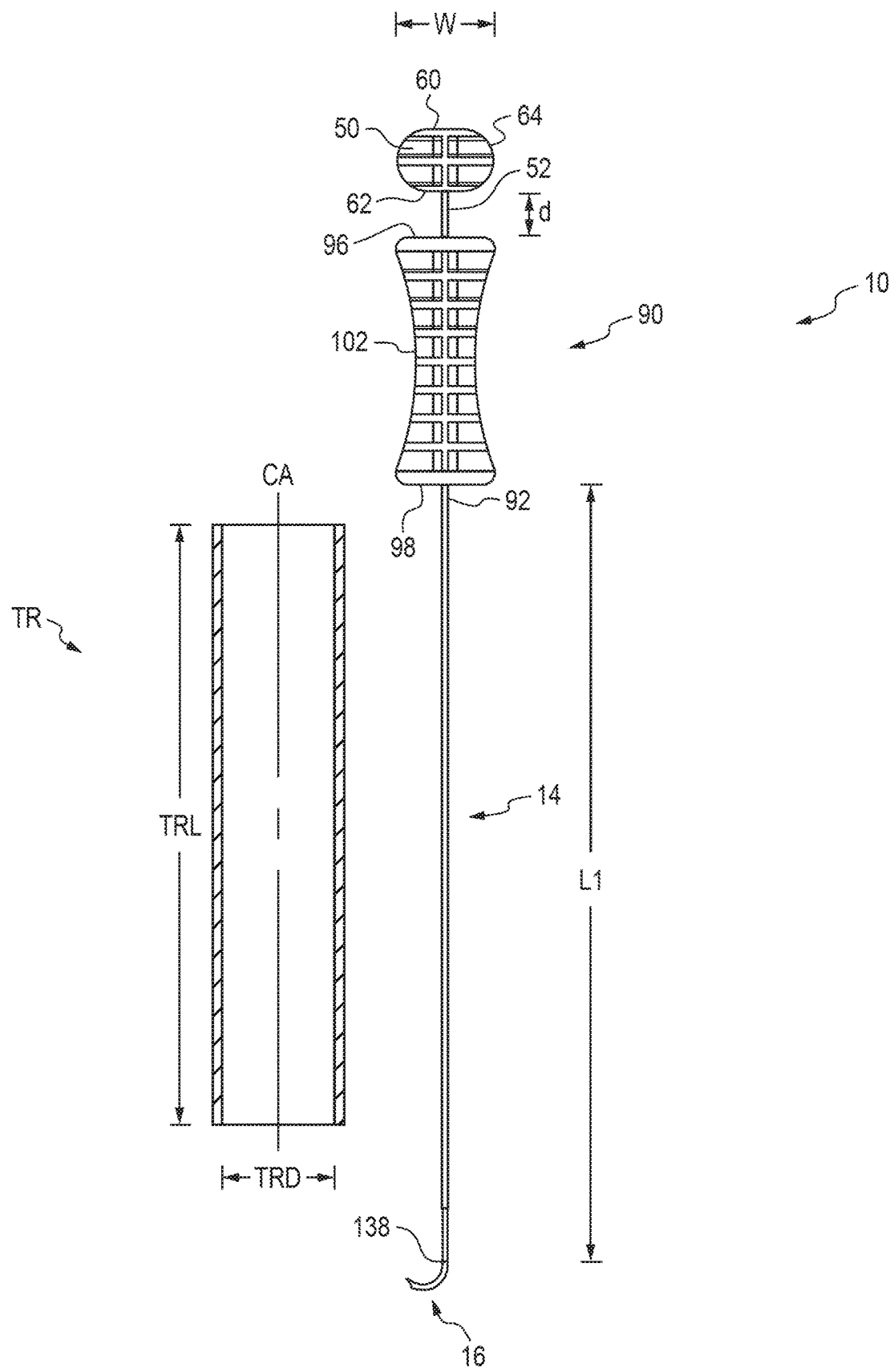
FIG. 9 is a side view of the suturing device of FIG. 1 next to a tubular retractor shown in cross section.

The maximum outer diameter of the handle 90, which can also be referred to as a width measured perpendicular to the longitudinal axis 56 since the handle need not be circular in a cross section normal to the longitudinal axis, can be 10-20 mm. In the illustrated embodiment, the handle 90 has a width W measured perpendicular to the longitudinal axis of less than 12 mm. FIG. 9 depicts a tubular retractor TR in cross section next to the suturing device 10 having a length TRL and an internal diameter TRD. Common tubular retractors used during minimally invasive spinal surgery procedures have inner diameters (e.g., depicted as the internal diameter TRD in FIG. 9) measuring between 14 mm to 22 mm. The maximum width of the handle 90 is not too large, which could impede the line of sight for the surgeon during a surgical procedure, especially when the surgeon is working through a tubular retractor or another small surgical portal other than a tubular retractor. As seen in FIG. 9, the button 50 also has a maximum width equal to the maximum width of the handle 90. It is also desirable to limit the maximum width of the button 50 so as not to impede the line of sight for the surgeon during a surgical procedure. As such, the maximum width of the button 50 measured perpendicular to the longitudinal axis 56 can be between 90% and 110% of the maximum width of the handle 90.

The handle 90 can be other shapes. For example, the handle could be in the form of a pistol grip, if desired.

With reference back to the illustrated embodiment and with reference to FIG. 9, the button 50 is offset from the handle 90 when the actuator 12 is in the first operating position. More particularly, the handle contact surface 62 of the button 50 is offset from the proximal end surface 96 of the handle 90 a distance d as measured parallel to the longitudinal axis 56. The distance d can be configured such that the distal end 70 of the actuator 12 remains inside the needle holder 16 when the actuator 12 is in the second operating position, which can be when the handle contact surface 62 of the button 50 contacts the proximal end surface 96 of the handle 90. If desired, the distance d can be configured such that the distal end 70 of the actuator 12 extends from the needle holder 16 when the actuator 12 is in the second operating position.

With reference back to FIG. 1, the elongate body 14 in the illustrated embodiment is in the form of a cannula. With reference to FIG. 2, the elongate body 14 has an outer surface 118, which is smooth, and defines a track 120 that receives a portion of the actuator 12. In the illustrated embodiment, the elongate body 14 is a cannula and the track 120 is a lumen that receives the tube 52 and the wire 54 of the actuator 12. The elongate body 14 can take other configurations, for example the track need not encircle the tube 52 and the wire 54, but could be U-shaped. In the illustrated embodiment, the elongate body 14 is circular in a cross section taken normal to the longitudinal axis 56, however, the elongate body 14 could take alternative configurations, such as polygonal or U-shaped in a cross section taken normal to the longitudinal axis 56. The elongate body 14 includes the proximal end portion 92 and a distal end portion 122. In the illustrated embodiment, the needle holder 16 is received in and connected with the elongate body 14 and extends away from the distal end portion 122. Alternatively, the needle holder 16 can be provided as part of the distal end portion 122 of the elongate body 14. In the illustrated embodiment, the elongate body 14 is made from metal and extends along the longitudinal axis 56. The elongate body 14 in the illustrated embodiment is made from a rigid material; however, if desired at least a portion of the elongate body 14 may be made from a malleable or flexible material to allow the surgeon to bend at least a portion of the elongate body 14 into a desirable configuration for insertion into an animal body during a surgical procedure. In the illustrated embodiment, an outer diameter of the elongate body 14 is constant between the proximal end portion 92 and the distal end portion 122. The outer diameter can be less than 3.5 mm, which provides a very slim device to enhance the line of sight for a surgeon during the surgical procedure.

Figure 10:
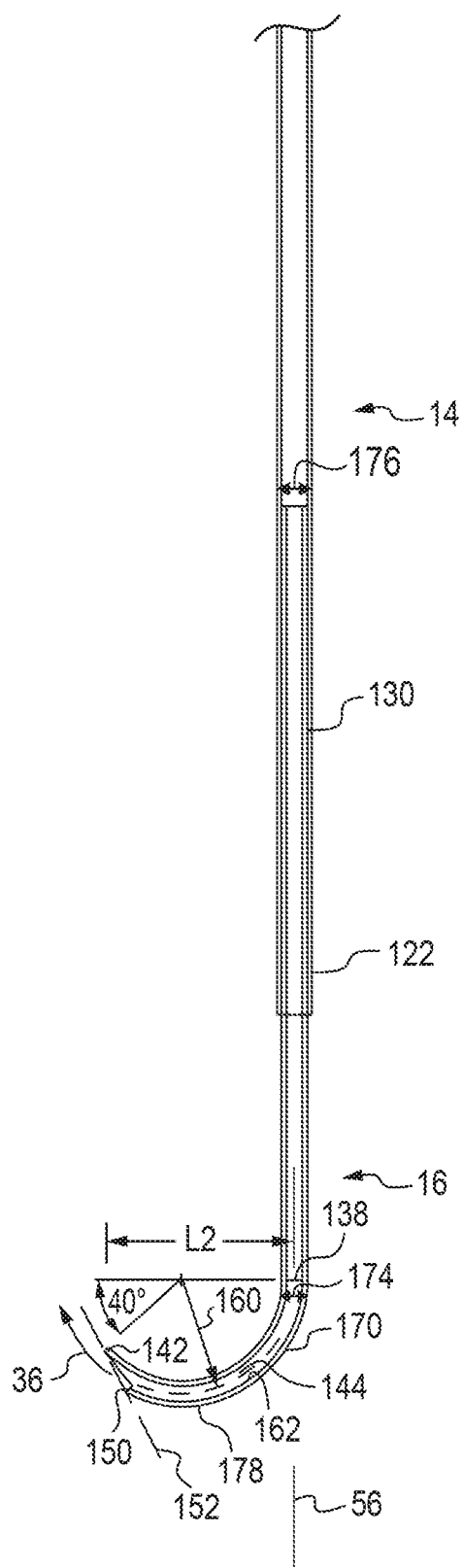
FIG. 10 is another cross-sectional view of the lower portion of the suturing device of FIG. 1.

The needle holder 16 extends away from the distal end portion 122 or is provided as part of the distal end portion 122 of the elongate body 14. With reference to FIG. 10, the needle holder 16 is a hollow tubular member. In the illustrated embodiment, a proximal end section 130 of the needle holder 16 that is aligned with the longitudinal axis 56 is received inside the elongate body 14; however, the needle holder 16 could be formed as part of the elongate body, e.g., both the elongate body 14 and the needle holder 16 could be made from one tubular stock material. In an alternative arrangement, the elongate body 14 and the needle holder 16 can be formed from elongate generally U-shaped in cross section material that are connected in a clam-shell type configuration. The needle holder 16 depicted in the illustrated embodiment is a curved needle holder that generally follows a constant radius such that the suturing device 10 can have J-hook configuration at a distal end thereof.

Figure 11:
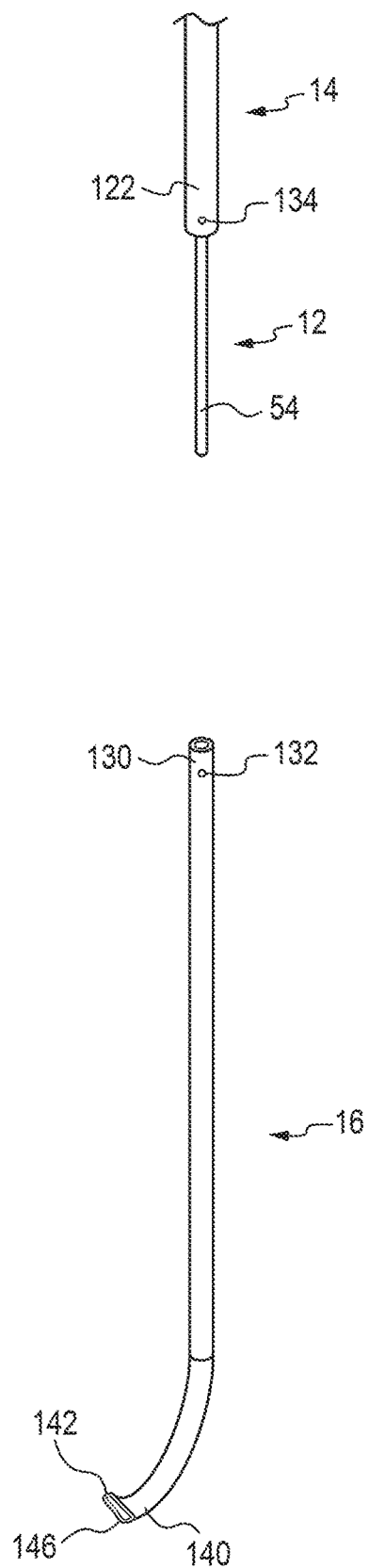
FIG. 11 is a perspective view of the lower portion of the suturing device of FIG. 1 showing a needle holder disconnected from an elongate body of the suturing device.

In the illustrated embodiment, the needle holder 16 is not intended to be removable from the elongate body 14; however, in an alternative arrangement the needle holder 16 can selectively connect with the elongate body 14 via a mechanical connection such as a friction fit or a bayonet connection. FIG. 11 shows the needle holder 16 separated from the elongate body 14. In such an embodiment, the needle holder 16 is releasably connected with the distal end portion 122 of the elongate body 14. For example, a protuberance 132 can be provided on the proximal end section 130 of the needle holder 16. The protuberance 132 fits into a recess 134 provided in the distal end portion 122 of the elongate body 14. A plurality of protuberances 132 and recesses 134 can be provided to releasably connect the needle holder 16 with the elongate body 14.

With reference back to FIG. 9, a distance L1, which is measured parallel with the longitudinal axis 56, from the distal end surface 98 of the handle 90 to a location 138 where the curved needle holder 16 begins to curve away from the longitudinal axis 56 is between 10 cm and 20 cm. Stated another way, the distance L1 measured parallel with the longitudinal axis 56 between where the curved needle holder 16 begins to curve away from the longitudinal axis 56 to where the elongate body 14 connects with the handle 90 is between about 10 cm to about 20 cm. In the illustrated embodiment, the distance L1 is about 13 cm. Common tubular retractors used during minimally invasive spine surgery have a length (e.g., depicted as the length TRL in FIG. 9) between 3 cm and 9 cm. The distance L1 allows the surgeon to insert the elongate body 14 and the needle holder 16 into the tubular retractor so that the needle holder 16 can contact the target tissue without the handle 90 contacting the tubular retractor while being close enough to the target tissue to allow the surgeon to manipulate the needle holder 16 without the suturing device being unwieldy. If the distance L1 is too long, manipulation of the needle holder 16 becomes more challenging.

With reference to FIGS. 10 and 11, the needle holder 16 includes a distal end section 140 having a distal-most tip 142. The needle holder 16 defines a needle passage 144 that is in communication with the track 120 and a distal opening 146. The distal opening 146 is offset from the longitudinal axis 56 in a forward direction. With reference to FIG. 10, the distal-most tip 142 is offset from the longitudinal axis 56 in a direction perpendicular from the longitudinal axis a distance L2 of less than 7 mm. As mentioned above, common tubular retractors used during minimally invasive spinal surgery procedures have diameters measuring between 14 mm to 22 mm. By spacing the distal-most tip 142 offset from the longitudinal axis 56 in a direction perpendicular from the longitudinal axis less than 7 mm, the surgeon can locate the elongate body 14 along the central axis CA of the tubular retractor and rotate the suturing device 10 around the central axis CA without contacting the side of the tubular retractor. The needle holder 16 could also be made from a malleable or flexible material to allow the surgeon to bend at least a portion of the needle holder 16 into a desirable configuration, e.g., around the distal-most tip 142 to help place the distal-most tip in the tissue tear.

In the illustrated embodiment, the distal end section 140 of the needle holder 16 is configured to allow the second end 32 of the needle 20 to release from the needle holder 16 at a location offset from the distal-most tip 142 in a direction opposite to the advance direction 36. The distal end section 140 of the needle holder 16 includes an offset edge 150 forming a part of a boundary of the distal opening 146 adjacent the location where the second end 32 of the needle 20 is released from the needle holder 16. With reference back to FIG. 2, as the needle 20 advances in the advance direction 36, the first end 30 of the needle 20 can pass through the target tissue 24 from an internal side 26 of the target tissue 24 toward an outer side 28 of the target tissue 24. The second end 32 of the needle 20, however, need not travel past the distal-most tip 142 of the needle holder 16 before being released from the needle holder 16. Such a configuration of the distal opening 146 facilitates loading of the needle 20 and the suture 22 into the needle passage 144, which occurs by inserting the second end 32 of the needle 20 into the distal opening 146 and moving the needle 20 with respect to the needle holder 16 in a direction opposite to the advance direction 36. The configuration of the distal opening 146 also mitigates the likelihood that the first end 30 of the needle 20 may pass through the suture 22 when being passed through the target tissue 24.

As more clearly seen in FIG. 11, the distal opening 146 is non-circular. With reference to FIG. 10, a line 152 intersects the offset edge 150 and the distal-most tip 142. The line 152 is offset from 90° with respect to a line drawn tangent to a point on the advance direction 36 where the advance direction intersects the line 152. As such, the distal opening 146 can be considered to be beveled. Even with the non-circular distal opening 146, when the needle 20 is in the retracted position (shown in FIG. 3), the first end 30 of the needle 20 is recessed inwardly (downwardly in FIG. 3) from the distal-most tip 142 within the needle passage 144. The distal-most tip 142 can also be rounded (see FIG. 11), which allows for the surgeon to grab or "hook" the target tissue 24 on the internal side 26 thereof and indent the target tissue 24 with the distal-most tip 142 while not catching the target tissue 24 with the first (pointed) end 30 of the needle 20. Also, a rounded ball could be provided at the distal-most tip 142. This allows the suturing device 10 to be used similar to a nerve hook, which is used in known surgical procedures.

Figures 17, 17A:
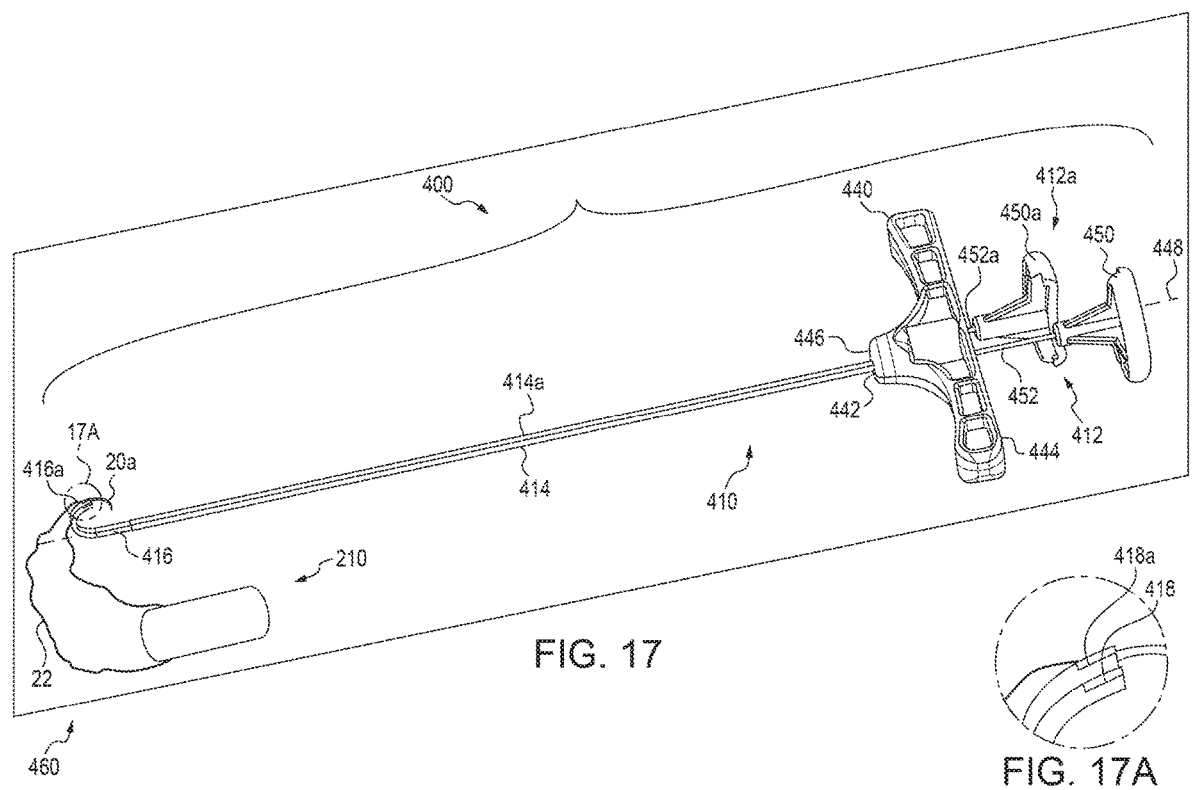
FIG. 17 is an alternative embodiment of a suturing device.
FIG. 17A is an enlarged view of the circled portion in FIG. 17.

The distal end section 140 of the needle holder 16 can be configured in other configurations to allow the second end 32 of the needle 20 to release from the needle holder 16 at a location offset from the distal-most tip 142. For example, a notch, which is depicted in FIG. 17, can be provided near the distal-most tip 142. The configuration of the distal end section 140 not only facilitates deployment of the needle 20 from the suturing device 10, but it also facilitates loading the needle 20 and the suture 22 into the suturing device 10.

Figure 16:
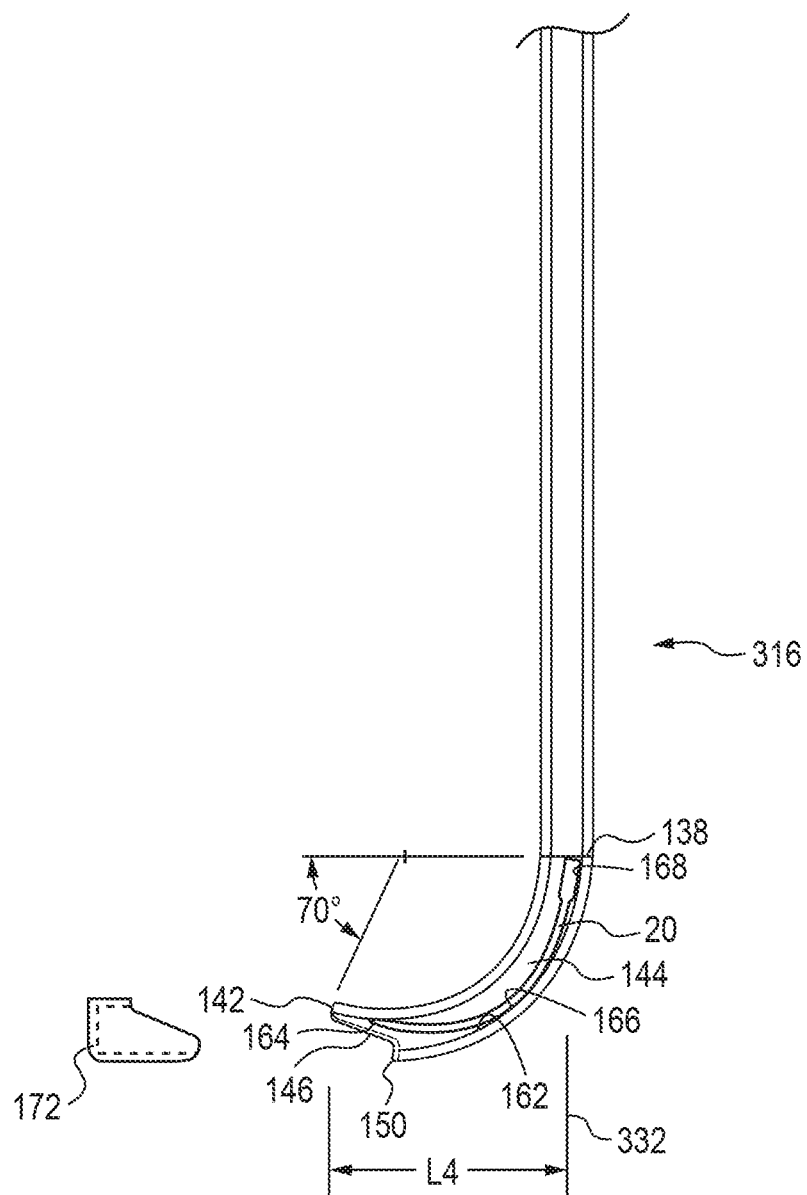
FIG. 16 is a cross-sectional view of the lower portion of the variation of the needle holder shown in FIG. 15.

With reference to FIG. 10, the needle passage 144 in the illustrated embodiment is curved and follows a curved needle passage radius 160, which is measured along a midline of the needle passage 144. The curved needle radius 34 for the curved needle 20 depicted in FIG. 2, and the curved needle passage radius 160 are similar, but need not be identical. By not matching the curved needle radius 34 to the curved needle passage radius 160, the needle 20 may contact an inner surface 162 of the needle holder 16 along a portion of its travel path in the needle holder 16 as the needle 20 moves from the retracted position toward the released condition. The needle 20 may contact the inner surface 162 of the needle holder 16 along a majority of its travel path in the needle holder 16 as the needle 20 moves from the retracted position toward the released condition. By not having the curved needle radius 34 match the curved needle passage radius 160, friction between the needle 20 and the inner surface 162 of the needle holder 16 helps retain the needle 20 in the needle holder 16, for example during transport. When the needle 20 is in the retracted position, the needle 20 can be in contact with the inner surface 162 of the needle holder 16 in at least three different locations along the length, or arc length, of the needle 20, e.g., a first location 164, a second location 166 and a third location 168, which are depicted in FIG. 16. The first location 164 is located beneath and adjacent to the distal-most tip 142. The second location 166 is located near the middle of the arc length of the needle 20. The third location 168 is located adjacent the location 138 where the curved needle holder 16 begins to curve away from the longitudinal axis 56. Also, the needle 20 can have a maximum outer diameter that is at least 40% of the inner diameter of the needle passage 144, which can facilitate retaining the needle 20 within the needle passage 144. Also, the needle 20 can have an outer diameter that is not greater than 90% of the inner diameter of the needle passage 144, which can allow the needle passage 144 to accommodate both the needle 20 and the suture 22.

The inner surface 162 of the needle holder 16 may be electro-polished to facilitate advancement of the needle 20 from the retracted position toward the released condition. Furthermore, a gel or other lubricant can be provided in the needle passage 144. The gel or lubricant can help retain the needle 20 in the needle passage 144 of the needle holder 16 and also decrease friction between the needle 20 and the inner surface 162 during deployment of the needle 20 from the suturing device 10. With reference to FIG. 16, a needle retainer 172 can be provided to retain the needle 20 in the needle passage 144 after manufacturing and before use, e.g., during shipment. The needle retainer 172 can be made from foam or a similar resilient material and covers the distal opening 146. It can be desirable to make the needle retainer 172 from an open cell foam to aid in the sterilization process. The needle retainer 172 can be inserted into the distal opening 146, or the needle retainer 172 can include a receptacle (shown in phantom in FIG. 16) and fit over the needle holder 16 to cover the distal opening 146. Where the suturing device 10 is packed with a backer card that retains the suturing device 10, the needle retainer 172 can be attached directly to or integrated into the backer card.

In an alternative arrangement, the wire 54 of the actuator 12 can also be pre-biased along a curve similar in radius to the curved needle passage radius 160 to facilitate deployment of the needle 20. As mentioned above, the pocket 76 (FIG. 7) or a similar device could be formed from a resilient material that clamps onto the second end 32 of the needle 20 while the needle 20 is being advanced through the needle holder 16 in the advance direction 36. For example, the pocket 76 (or similar device) can have an outer diameter such that the inner surface 162 applies a force to the pocket 76 so that the pocket 76 frictionally engages the second end 32 of the needle 20 until the needle 20 is in the released condition, i.e., fully released from the needle holder 16. As such, the pocket 76 (or similar device) at the distal end 70 of the actuator 12 selectively connects with and disconnects from the needle 20, which allows the surgeon to retract the needle 20 back into the needle holder 16 after the needle 20 has been moved in the advance direction 36 but prior to the needle 20 obtaining the released condition.

In the illustrated embodiment, the needle holder 16 defines the distal extent of the suturing device 10. An outer diameter 174, which need not be circular, of the needle holder 16 is about equal to or less than an outer diameter 176 of the distal end portion 122 of the elongate body 14. Also, the outer diameter 174 of the needle holder 16 is constant, or nearly constant, from the distal-most tip 142 to where the needle holder 16 transitions to the elongate body 14. The distal extent of the suturing device 10 is at a point 178 along the needle holder 16, which is curved in the illustrated embodiment, where a tangent line at that point 178 is perpendicular to the longitudinal axis 56. By providing a needle holder 16 having a constant or nearly constant outer diameter 174 with the distal extent of the suturing device 10 being at the point 178 on the outer surface 180 of the needle holder 16 where a tangent line is perpendicular to the longitudinal axis 56, a very slim suturing device 10 is provided that can reach just underneath the internal side 26 of the target tissue 24 (see FIG. 2) while avoiding nerves, which can be found in the dural sac.

The outer surface 180 of the needle holder 16 extends along a radius, which is equal in magnitude to the curved needle passage radius 160, and follows an arc length less than 180 degrees, and in the embodiment illustrated in FIG. 10 about 40 degrees less than 180 degrees (i.e., less than about 140 degrees), as measured from the location 138 where the curved needle holder 16 begins to curve away from the longitudinal axis 56 to the distal-most tip 142 of the needle holder 16. The needle holder 16 can extend along the radius an arc length greater than 90 degrees and less than 180 degrees, for example see also FIG. 16. This configuration also allows the suturing device 10 to operate similar to a nerve hook that is used in surgical procedures. The arc length of the needle holder 16 can be at least as long as the arc length of the needle 20. For example, the arc length of the needle holder 16 can be between 5-25% longer than the arc length of the needle 20, and in the depicted embodiments the arc length of the needle holder 16 is about 15% longer than the arc length of the needle 20. In another alternative arrangement, the needle holder 16 can extend along the radius an arc length greater than 20 degrees and less than 190 degrees.

As mentioned above, the distal opening 146 is offset from the longitudinal axis 56, which is the axis along which a majority of the actuator 12 travels in the illustrated embodiment when moving from the first operating position toward the second operating position. The illustrated suturing device 10 is a sleek device, which makes it useful to repairing dural sac tears. By way of example, consider a first plane in which both the longitudinal axis 56 and the curved needle passage radius 160 reside. This first plane is the plane in which the cross section was taken in FIG. 2. Consider a second plane, which is perpendicular to the first plane, parallel to the longitudinal axis 56 and intersects a line along the outer surface 118 of the elongate body 14 furthest from the distal-most tip 142. This second plane would be perpendicular to the page on which FIG. 2 is printed and would be offset to the right of the longitudinal axis 56 while intersecting a line along the outer surface 118 of the elongate body 14. In the illustrated embodiment, the working components of the suturing device 10 at the distal portion thereof are all forward (to the left in FIG. 2) of this second plane. For example, the distal end portion 122 of the elongate body 14 does not bend rearward (to the right in FIG. 2) of the second plane. Such a configuration is useful when the distal end portion 122 is being inserted through a tubular retractor, which is used in minimally invasive spine surgeries.

FIG. 3 depicts at least a portion of the suture 22 extending through the distal opening 146 when the needle 20 is received in the needle passage 144 and the actuator 12 is in the first operating position, which is shown in FIGS. 1 and 3. Allowing the suture 22 to extend through the distal opening 146 can be useful when the elongate body 14 or the needle holder 16 has a closed cross section with respect to the longitudinal axis 56. When the elongate body 14 or the needle holder 16 has an open cross section, e.g., U-shaped, however, the suture 22 may not extend through the distal opening 146; instead, the suture 22 can extend into and along the elongate body 14. With reference back to the illustrated embodiment, at least a portion of the suture 22 extends along the needle passage 144 from the second end 32 of the needle 20 toward the distal opening 146 between the needle 20 and the inner surface 162 of the needle holder 16 when the needle 20 is received in the needle passage 144 and the actuator 12 is in the first operating position.

With reference to FIG. 4, by having the suture 22 extend from the distal opening 146 of the needle holder 16, a double-armed suture can be used with the suturing device 10. For example, FIG. 4 shows the suture 22 being a double-armed suture having the needle 20, which will also be referred to as the first needle, at a first end of the suture 22 and a second needle 20a at a second, opposite, end of the suture 22. The first needle 20 is loaded into the suturing device 10, which will hereinafter be referred to as the first suturing device, and the second needle 20a is loaded into an identical suturing device 10a, which will be referred to as the second suturing device 10a.

Figure 12:
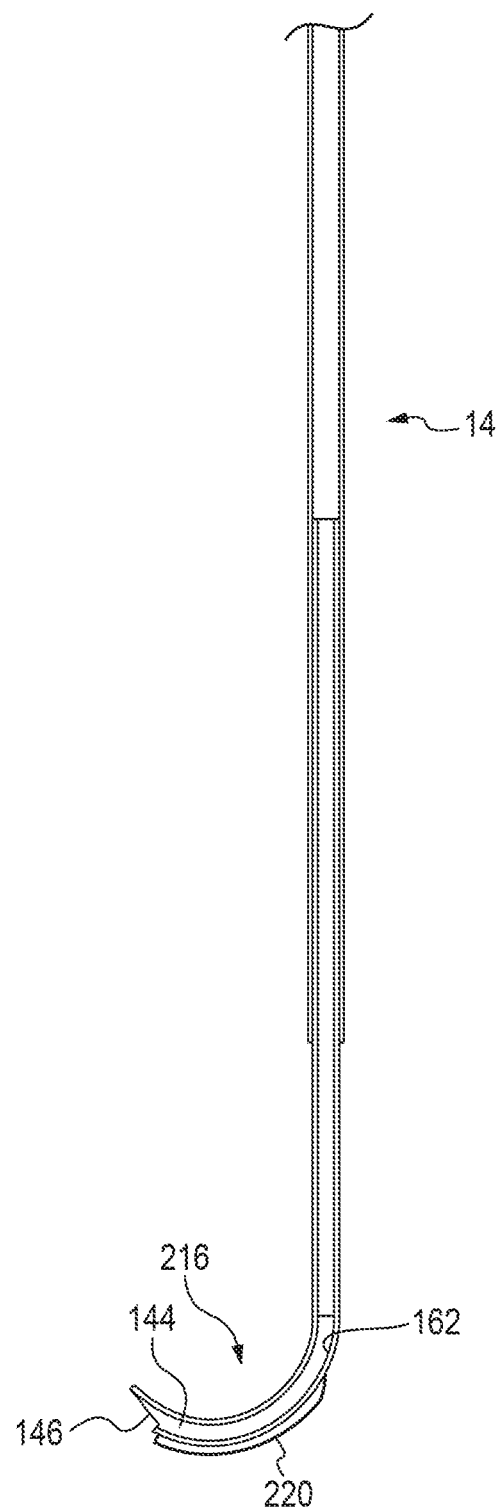
FIG. 12 is a schematic cross-sectional view of the lower portion of a variation of the needle holder of the suturing device of FIG. 1.

FIG. 12 shows a variation from the needle holder 16 described above, in which a needle holder 216 includes a keyway 220. Other than the addition of the keyway 220, the needle holder 216 can be identical to the needle holder 16. As such, where the needle holder 216 is identical or very similar to the needle holder 16, the same reference numbers will be used. The keyway 220 is offset from the needle passage 144. At least a portion of the suture 22 (see FIG. 3) can extend along the keyway 220 from the second end 32 of the needle 20 toward the distal opening 146 between the needle 20 and the inner surface 162 of the needle holder 16 when the needle 20 is received in the needle passage 144 and the actuator 12 is in the first operating position. The keyway 220 can provide a space for the suture 22 and can be appropriately shaped so that the needle 20 would not fit into the keyway 220, but instead would be maintained within the needle passage 144, which is located above the keyway 220 as illustrated in FIG. 12.

Figure 13:
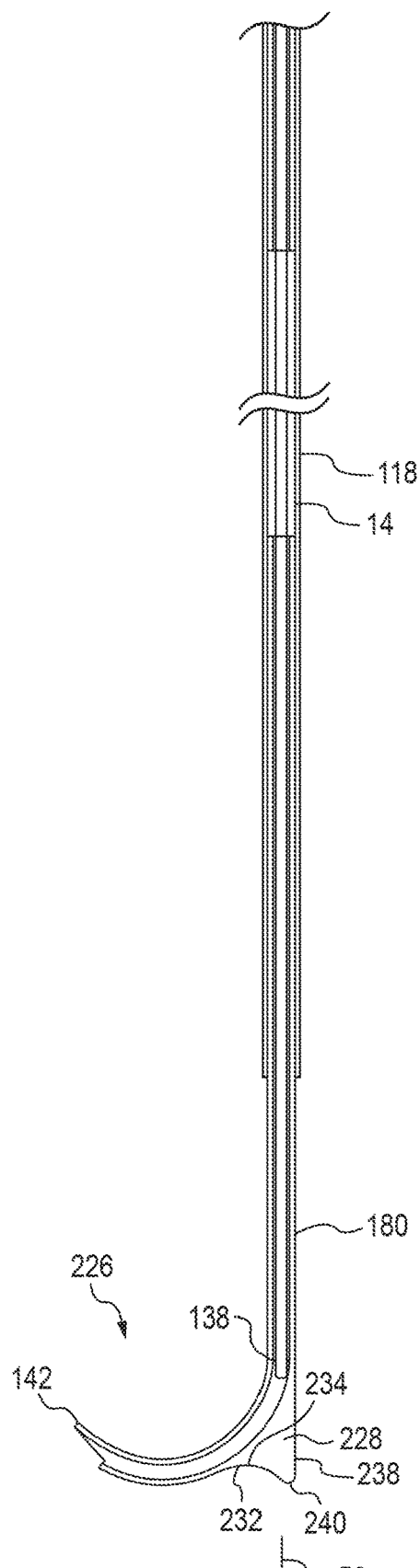
FIG. 13 is a cross-sectional view of the lower portion of another variation of the needle holder of the suturing device of FIG. 1.
Figure 14:
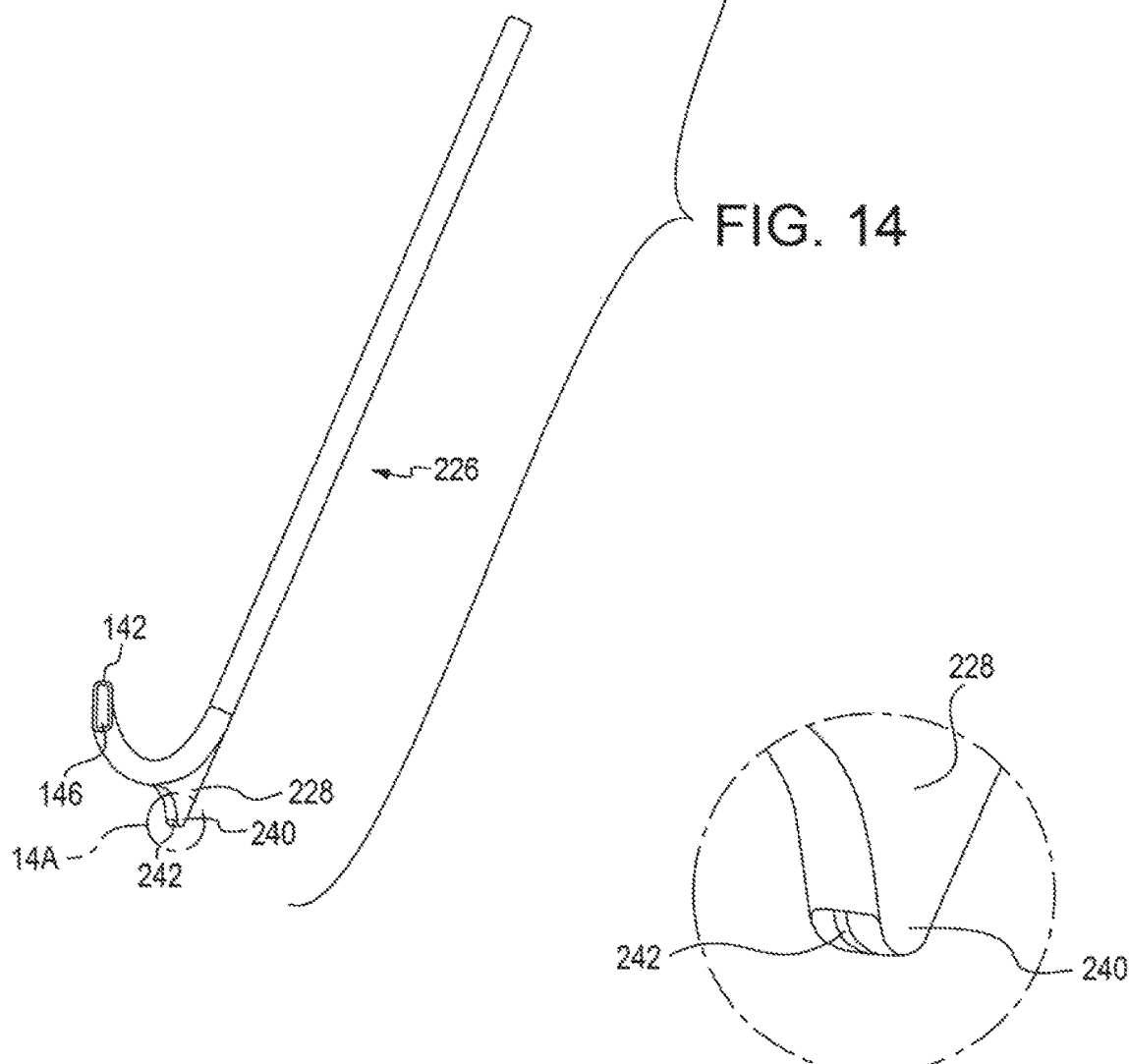
FIG. 14 is a perspective view of a lower portion of the suturing device showing the variation of FIG. 13.
Figure 14A:
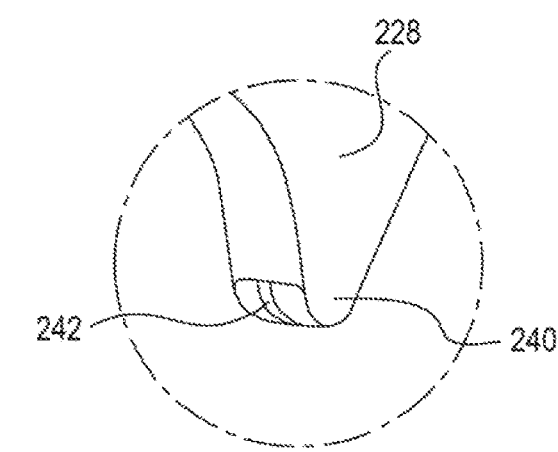
FIG. 14A is an enlarged view of the circled portion in FIG. 14.

FIGS. 13 and 14 show another a variation from the needle holder 16 described above, in which a needle holder 226 includes a knot pusher 228. Other than the addition of the knot pusher 228, the needle holder 226 can be identical to the needle holder 16. As such, where the needle holder 226 is identical or very similar to the needle holder 16, the same reference numbers will be used. In the variation shown in FIGS. 13 and 14, the suturing device 10 includes the knot pusher 228 connected with and extending away from at least one of the elongate body 14 and the needle holder 226. In the illustrated embodiment, the knot pusher 228 is formed as part of the needle holder 226. With reference to FIG. 14, the needle holder 226 can be releasably connected with the distal end portion 122 of the elongate body 14. Also, the knot pusher 228 could also be made as a separate component that is releasably connected with at least one of the elongate body 14 and the needle holder 226.

In the embodiment illustrated in FIGS. 13 and 14, the knot pusher 228 includes a lower concave surface 232. The lower concave surface 232 is configured to be pressed down against a knot tied in the suture 22 to slide the knot toward the tissue that is being sewed by the surgeon. The lower concave surface 232 includes an inflection 234 offset from the longitudinal axis 56 of the elongate body 14 in the same direction that the distal-most tip 142 is offset from the longitudinal axis 56.

The knot pusher 228 is generally triangular in shape when viewed from the side as shown in FIG. 13. More particular to the illustrated embodiment, the knot pusher 228 extends from the outer surface 180 of the needle holder 226, and the outer surface 180 is curved. The knot pusher 228 also includes an external side surface 238. The external side surface 238 extends along a plane parallel to and offset from the longitudinal axis 56 of the elongate body 14 between the location 138 where the needle holder 226 begins to curve away from the longitudinal axis 56 to a corner 240, which can be rounded. The maximum distance, which is measured perpendicular to the longitudinal axis 56 of the elongate body 14, between the external side surface 238 and the distal-most tip 142 is less than 10 mm, which allows the suturing device 10 to fit nicely in the common tubular retractors described above. As discussed above, consider the first plane in which both the longitudinal axis 56 and the curved needle passage radius 160 (see FIG. 10) reside. This first plane is the plane in which the cross section was taken in FIG. 13. Consider a second plane, which is perpendicular to the first plane, parallel to the longitudinal axis 56 and intersects a line along the outer surface 118 of the elongate body 14 furthest from the distal-most tip 142. This second plane would be perpendicular to the page on which FIG. 13 is printed and would be offset to the right of the longitudinal axis 56 while intersecting a line along the outer surface 118 of the elongate body 14. In the illustrated embodiment, no portion of the knot pusher 228 extends in a direction away from the distal-most tip 142 beyond the second plane. This is beneficial in that when the surgeon is working on one side or a tissue tear (e.g., the left side in FIG. 2), the knot pusher 228 is unlikely to catch on the opposite (the right side in FIG. 2) side of the tissue tear.

With reference to FIG. 14, a recess 242, which can be somewhat similar in configuration to a claw hammer, could be provided in the knot pusher 228 at the corner 240. Similar to the lower concave surface 232, the recess 242 could be configured to be pressed down against a knot tied in the suture 22 to slide the knot toward the tissue that is being sewed by the surgeon.

Figure 15:
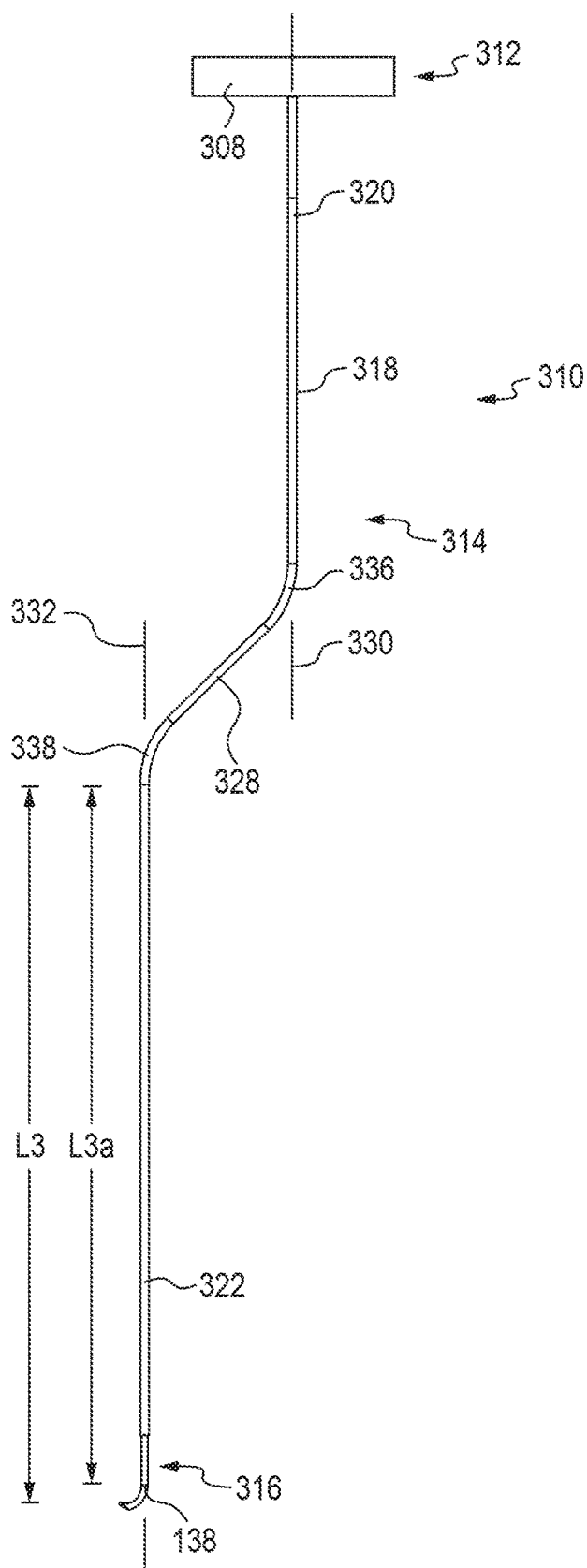
FIG. 15 is a side view showing a variation of the elongate body and a variation of the needle holder of the suturing device.

FIGS. 15 and 16 show a variation of a suturing device 310 from the suturing device 10 described above. In this variation, an actuator 312 differs from the actuator 12 by being configured to connect with or be provided as part of an end effector of a robot, an elongate body 314 differs from the elongate body 14 by having a bayonet configuration and a needle holder 316 differs from the needle holder 16 by having smaller arc length.

The actuator 312 can include the tube 52 (or rod) and the wire 54 as described above, however, the actuator 312 need not include the button 50 described above. The tube 52 (or rod) and the wire 54 moves with respect to the elongate body 14 in the same manner as described above, however, instead of moving the button 50 to move the tube 52 (or rod) and the wire 54, a robot (not shown) can attach with the actuator 312 such that the suturing device 310 operates as an end effector for the robot. The actuator 312 includes an actuator body 308 that can attach to a robot wrist (for example) and the robot can be programmed to operate with the suturing device 310 to suture the target tissue. When the actuator body 308 is attached to the robot, the robot can move the tube 52 (or rod) and the wire 54 with respect to the elongate body 14 in the same manner as described above.

With reference to FIG. 15, the elongate body 314 in the illustrated embodiment is in the form of a cannula, which is similar to the elongate body 14. The elongate body 314 has an outer surface 318, which is smooth, and defines a track (not visible in FIG. 15 or 16, but similar to the track 120) that receives a portion of the actuator 312. Similar to the embodiment described above, the elongate body 314 is a cannula and the track is a lumen that receives the tube 52 and the wire 54 of the actuator 312. The track need not encircle the tube 52 and the wire 54, but could be U-shaped. In the embodiment in FIG. 15, the elongate body 314 is circular in a cross section taken normal to the longest dimension of the elongate body 314, however, the elongate body 314 could take alternative configurations, such as polygonal or U-shaped.

The elongate body 314 includes the proximal end portion 320 and a distal end portion 322. The proximal end portion 320 connects with the actuator body 308, or, if desired, the proximal end portion 320 can connect with the handle 90 in the same manner that the elongate body 14 connects with the handle 90. In the embodiment where the proximal end portion 320 connects with the handle 90, the button 50 can connect with the tube 52 (or rod) similar to that shown in FIGS. 8 and 8A, and the actuator 312 can operate in the same manner as the actuator 12 described above. Also, a pistol-grip style handle could attach to the elongate body instead in of the actuator body 308.

As illustrated in FIG. 15, the needle holder 316 is received in and connected with the elongate body 314 and extends away from the distal end portion 322. Alternatively, the needle holder 316 can be provided as part of the distal end portion 122 of the elongate body 314. The elongate body 314 is made from a rigid metal material; however, if desired at least a portion of the elongate body 314 may be made from a malleable or flexible material to allow the surgeon to bend at least a portion of the elongate body 314 into a desirable configuration for insertion into an animal body during a surgical procedure. In the illustrated embodiment, an outer diameter of the elongate body 314 is constant between the proximal end portion 320 and the distal end portion 322. The outer diameter can be less than 3.5 mm, which provides a very slim device to enhance the line of sight for a surgeon during the surgical procedure.

The elongate body 314 has a bayonet configuration. The elongate body 314 includes an intermediate portion 328 positioned between the proximal end portion 320 and the distal end portion 322. The proximal end portion 320 extends along a proximal end portion longitudinal axis 330. The distal end portion 322 extends along a distal end portion longitudinal axis 332, which is offset from the proximal end portion longitudinal axis 330 in a forward direction. In the illustrated embodiment, the distal end portion longitudinal axis 332 is offset from the proximal end portion longitudinal axis 330 about 25 mm. The proximal end portion 320 transitions to the intermediate portion 328 through a proximal bend 336 and the intermediate portion 328 transitions to the distal end portion 322 through a distal bend 338. In the illustrated embodiment, the proximal bend 336 and the distal bend 338 are both angled internally 135 degrees.

A distance L3, which is measured parallel with the distal end portion longitudinal axis 332, between where the distal bend 338 transitions to the distal end portion 322 (i.e., the proximal end of the distal end portion 322 on the distal end portion longitudinal axis 332) and the distal-most tip 142 is between 10 cm and 20 cm. Also, a distance L3a, which is measured parallel with the distal end portion longitudinal axis 332, between where the distal bend 338 transitions to the distal end portion 322 to the location 138 where the needle holder 316 begins to curve away from the distal end portion longitudinal axis 332 is between 10 cm and 20 cm. Stated another way, the distance L3a measured parallel with the distal end portion longitudinal axis 332 between where the curved needle holder 16 begins to curve away from the distal end portion longitudinal axis 332 to where the elongate body 314 begins to curve away from the distal end portion longitudinal axis 332 (e.g., near the proximal end of the distal end portion 322 on the distal end portion longitudinal axis 332) is between about 10 cm to about 20 cm. In the illustrated embodiment, the distance L3 is about 12.5 cm and the distance L3a is about 12 cm. The distances L3 and L3a allow the surgeon to insert the distal end portion 322 of the elongate body 314 and the needle holder 316 into a commonly used tubular retractor so that the needle holder 316 can contact the target tissue without the intermediate portion 328 and the proximal end portion 320 entering the tubular retractor. If the distances L3 and L3a are too long, manipulation of the needle holder 316 becomes more challenging. The proximal end portion 320 is offset from the distal end portion 322 in a rearward direction, which is opposite to the direction that the distal-most tip 142 is offset from the distal end portion 322. This offsets the handle 90 (not shown in FIG. 15, but could be connected with the elongate body 314 anywhere along the proximal end portion 320) from the distal end portion longitudinal axis 332, which results in the surgeon's hand and the handle 90 not impeding line of sight through the tubular retractor.

FIGS. 15 and 16 show a variation from the needle holder 16 described above, in which the needle holder 316 has a smaller arc length than the needle holder 16. Other than having a smaller arc length, the needle holder 316 can be identical to the needle holder 16. As such, where the needle holder 316 is identical or very similar to the needle holder 16, the same reference numbers will be used. With reference to the variation of the needle holder 316 shown in FIG. 16, the distal-most tip 142 is offset from the distal end portion longitudinal axis 332 in a direction perpendicular from the distal end portion longitudinal axis 332 a distance L4 of less than 5 mm. The needle holder 316 extends along a radius about 110 degrees from the location 138 where the needle holder 316 begins to curve away from the distal end portion longitudinal axis 332 to the distal-most tip 142. Since the needle holder 316 has a smaller arc length than the needle holder 16, the first end 30 of the needle 20 (see FIGS. 2 and 3) may extend outwardly beyond the distal opening 146 when the needle 20 is in the retracted position (shown in FIG. 3). The first end 30, however, does not extend beyond the distal-most tip 142 when in the retracted position (similar to what is shown in FIG. 3). Accordingly, the suturing device 10 having the needle holder 316 can still be used similar to a nerve hook while not catching the target tissue 24 with the first (pointed) end 30 of the needle 20.

FIG. 4 shows one example of a suturing kit 200 that can be provided including a double-armed suture 22, at least one suturing device 10, 10a and a suture holding structure 210. The second suturing device 10a is identical in all aspects to the first suturing device, and therefore will not be described in detail. The suture holding structure 210 can be similar to a known racetrack, which is typically used to hold a suture. A knot pusher 350 can also be provided in the suturing kit 200. Also, additional needle holders, for example, the needle holder 16b shown in FIG. 4, can also be provided in the kit 200. These additional needle holders, e.g., the needle holder 16ba and other needle holders (not shown) can be loaded with additional curved needles (similar to the curved needle 20) and additional sutures (similar to the suture 22). Also, surgical patches 352 could be provided, which can be connected to a suture 22 extending from a needle holder, such as the needle holder 16b, could also be provided in the kit 200. FIG. 17 depicts another example of a suturing kit 400 that can be provided including the double-armed suture 22, at least one suturing device 410 and the suture holding structure 210. In the embodiment shown in FIG. 4, the first suturing device 10 and the second suturing device 10a are separate instruments from one another. In contrast, in the embodiment shown in FIG. 17, the suturing device 410 can have a double-barrel design. Moreover, multiple suturing devices can be provided in each kit along with multiple suture holding structures.

With reference to FIG. 17, the suturing device 410 includes a first actuator 412, a second actuator 412a, a first elongate body 414, a second elongate body 414a, a first needle holder 416 and a second needle holder 416a. The suturing device 410 shown in FIG. 17 is also useful during a surgical procedure to accurately locate a first needle 20 (not visible in FIG. 17, but located inside the first needle holder 416 in a similar manner to that shown in FIG. 2), the second needle 20a and the suture 22 with respect to target tissue, similar to the target tissue 24 shown in FIG. 2, which is to be sutured. The needles 20, 20a shown in FIG. 17 have been described above. Each needle holder 416, 416a can be identical to the needle holder 16 described above. However, in the embodiment depicted in FIG. 17, the first needle holder 416 is positioned adjacent to and connected with the second needle holder 416a. Also, each needle holder 416, 416a includes a respective notch 418, 418a, which can facilitate release of the needles 20, 20a from the needle holders 416, 416a and loading of the needle into the needle holders. The first needle holder 416 can be welded, glued or mechanically fastened to the second needle holder 416a. Each elongate body 414, 414a can be identical to the elongate body 14 described above. However, in the embodiment depicted in FIG. 17, the first elongate body 414 is positioned adjacent to and connected with the second elongate body 414a. The first elongate body 414 can also be welded, glued or mechanically fastened to the second elongate body 414a.

The suturing device 410 also includes a handle 440 connected with the elongate bodies 414, 414a. Similar to the handle 90 described above, the handle 440 connects with a proximal end portion of each elongate body 414, 414a and is fixed to each elongate body 414, 414a such that movement of the handle 440, e.g., rotational or translational movement, results in the same movement of each elongate body 414, 414a. The handle 440 includes an elongate bore 442 in which the proximal end section of each elongate body 414, 414a is received. The handle 440 takes an alternative configuration as compared to the handle 90 described above and is generally T-shaped. The elongate bore 442 extends from a proximal end surface 444 to a distal end surface 446 and is aligned with a longitudinal axis 448 that is parallel with a longest dimension of each elongate body 414, 414a.

Each actuator 412, 412a operates similarly to the actuator 12 described above. The first actuator 412 includes a button 450, a tube 452, which could also be a rod, and a wire, which is not visible in FIG. 17 but is similar to the wire 54 described above. Similarly, the second actuator 412a includes a button 450a, a tube 452a, which could also be a rod, and a wire, which is not visible in FIG. 17 but is similar to the wire 54 described above.

The first actuator 412 is identical to the second actuator 412a. Accordingly, the first actuator 412 will be described in detail with respect to the first elongate body 414 and the first needle holder 416 with the understanding that the second actuator 412a cooperates with the second elongate body 414a and the second needle holder 416a in the same manner. The first tube 452 (or rod) and the first wire (not visible) of the first actuator 412 is received within the first elongate body 414 and moves with respect to the first elongate body 414 between the first operating position and the second operating position, similar to the actuator 12 described above. The first tube 452 moves in a direction parallel with the longitudinal axis 448. The wire (not visible) contacts the second end 32 (see FIG. 2) of the first needle 20 to advance the needle 20 from the retracted position toward the released condition. The buttons 450, 450a differ from the button 50 described above, however, the actuators 412, 412a can operate in the same manner as the actuator 12 described above. Therefore, the operation of the actuators 412, 412a will not be described in further detail.

Both FIGS. 4 and 13 disclose suturing kits including a double-armed suture, at least one suturing device and a suture holding structure. In both embodiments, the at least one suturing device includes a portion configured to be inserted into a patient.

In the embodiment depicted in FIG. 4, the first needle holder 16 and the first elongate body 14 are part of a first suturing device 10, which is a physically separate device from the second suturing device 10a. The second suturing device 10a is, however, loaded with the second needle 20a and the suture 22 in a similar manner to that shown in FIG. 2 so that a double-armed suture is connected with both suturing devices 10, 10a. Instead of providing the second suturing device 10a shown in FIG. 4, the suturing kit could include the actuator 12, the elongate body 14 and at least two needle holders 16 where the needle holders are disconnected from the elongate body 14, similar to what is shown in FIG. 11. Alternatively, one of the needle holders 16 could be connected with the elongate body 14 and additional needle holders 16, which can be loaded with a respective needle 20 and suture 22, can also be provided with the kit. In the embodiment depicted in FIG. 17, the first needle holder 416, the first elongate body 414, the second needle holder 416a, the second elongate body 414a are all part of the same suturing device 410.

In each of the aforementioned embodiments, the suture holding structure 210 holds at least a portion of the suture 22 between the first end and the second end of the suture 22. In both embodiments, the suture holding structure 210 is separate from the at least one suturing device, e.g. the suturing devices 10, 10a or the suturing device 410, so as not to be inserted into the patient during the surgical procedure. In other words, the suture holding structure 210, and thus much of the suture, remains outside of the patient during the surgical procedure. Both the kit 200 shown in FIG. 4, the kit having another needle holder disconnected from the elongate body 14, and the kit 400 shown in FIG. 17 can be provided with a sealed package 460 (only schematically depicted in FIG. 17), which contains the suture 22, the at least one suturing device, e.g. the first suturing device 10 and the second suturing device 10a in FIG. 4 or the suturing device 410 in FIG. 17, and the suture holding structure 210.

A method of operating a suturing device to repair a tissue tear will be described with reference to the suturing devices 10, 10a and 410 described above; however, the method may be practiced using differently configured suturing devices and/or the variations shown in FIGS. 12-16, and these variations may be referred to below where relevant. The physician can insert the suturing device 10 into a tubular retractor, such as the tubular retractor TR depicted in FIG. 9, or into another small surgical portal. With reference to FIG. 2, the physician can position the distal-most tip 142 of the suturing device 10 under the internal side 26 of the target tissue 24 on a first (left per the orientation of FIG. 2) side of a tear through the target tissue 24. The target tissue 24 depicted in FIG. 2 is a dural sac, which is a sheath of dura mater that surrounds the spinal cord, which is not shown in FIG. 2 for purposes of clarity. With the distal-most tip 142 under the internal side 26 of the target tissue 24, the physician then actuates the actuator 12 on the suturing device 10 to advance the first end 30 of the needle 20 through the target tissue 24 from the internal side 26 toward the outer side 28 until the second end 32 of the needle 20 and the suture 22 are released from the suturing device 10. The physician can then remove the suturing device 10 from inside the patient (and inside the dural sac) and grasp the needle 20 and pull the suture 22 through the hole that was formed in the target tissue 24 with the needle 20. The physician can then take another suturing device, for example, the second suturing device 10a shown in FIG. 4, which has the second needle 20a loaded in it and the opposite end of the suture 22 attached to the second needle 20a and insert the second suturing device 10a into the tubular retractor TR (FIG. 9) or other small surgical portal. The physician can position the distal-most tip of the second suturing device 10a, which is the same as the distal-most tip 142 depicted in FIG. 2, under the internal side 26 of the target tissue 24 on a second (right per the orientation of FIG. 2) side of the tear through the target tissue 24. With the distal-most tip of the second suturing device 10a under the internal side 26 of the target tissue 24, the physician then actuates the actuator 12a (FIG. 4) on the second suturing device 10a to advance the first (pointed) end of the second needle 20a through the target tissue 24 from the internal side 26 toward the outer side 28 until the second end of the second needle 20a and the suture 22 are released from the second suturing device 10a. The physician can then remove the second suturing device 10a from inside the patient (and inside the dural sac) and grasp the second needle 20a and pull the suture 22 through the hole that was formed in the target tissue 24 with the second needle 20a. The physician can then tie a knot in the suture 22 in a conventional manner to close the tear, and this process can be repeated until the tear has been adequately closed.

Instead of using two different suturing device 10 and 10a, the physician may use only the first suturing device 10. In this example, the second needle 20a would still be connected to an opposite end of the suture 22 as the first needle 20; however, the second needle 20a would not be pre-loaded into a suturing device. Instead, the second needle 20a would be free from a suturing device, and the second needle 20a would be loaded into the first suturing device 10 after the first needle had been deployed from the first suturing device 10. So, the physician would deploy the first needle 20 from the suturing device 10 in the same manner as described above and remove the suturing device 10 from the patient. The physician would then pull the actuator 12 back to the first operating position from the second operating position. The second needle 20a having the suture 22 attached thereto would then be inserted through the distal opening 146 and into the needle passage 144 until the second needle 20a is in the retracted position, which is shown for the first needle 20 in FIG. 3. In an alternative arrangement, the actuator 12 can remain in the second operating position while the needle 20 is being loaded into the needle holder 16. For example, the actuator 12 could facilitate drawing the needle 20 into the retracted position. As one example, the pocket 76 (see FIG. 7) could grasp the second end 32 of the needle 20, and movement of the actuator 12 from the second operating position toward the first operating position could draw the needle 20 toward the retracted position. With reference back to the illustrated embodiment and like that shown in FIG. 3, a portion of the suture 22 would be maintained extending out of the distal opening 146 and outside of the suturing device 10. The physician would then operate the suturing device 10 with the second needle 20a loaded therein in a similar manner how the physician operated the second suturing device 10a above.

The physician could also use the suturing device 410 in a similar manner. The physician can position the distal-most tip, which is not particularly called out in FIG. 17 but could have a similar configuration to the distal-most tip 142 in FIG. 11, on the first needle holder 416 of the suturing device 410 under the internal side of the target tissue on a first (e.g., left) side of a tear through the target tissue. With the distal-most tip on the first needle holder 416 of the suturing device 410 under the internal side of the target tissue, the physician then actuates the first actuator 412 on the suturing device 410 to advance the first end of the first needle (not visible in FIG. 17 because it is loaded within the first needle holder 416) through the target tissue from the internal side toward the outer side until the second end of the first needle and the suture 22 are released from the suturing device 410. The physician can then rotate the suturing device 410 about the longitudinal axis 448 and position the distal-most tip on the second needle holder 416a of the suturing device 410 under the internal side of the target tissue on a second (e.g., right) side of the tear. With the distal-most tip on the second needle holder 416a of the suturing device 410 under the internal side of the target tissue, the physician then actuates the second actuator 412a on the suturing device 410 to advance the first end of the second needle 20a through the target tissue from the internal side toward the outer side until the second end of the second needle 20a and the suture 22 are released from the suturing device 410. The physician can then remove the suturing device 410 from inside the patient (and inside the dural sac) and grasp the needles 20, 20a and pull the suture 22 through the holes that were formed in the target tissue with the needles 20, 20a. The physician can then tie a knot in the suture 22 in a conventional manner to close the tear, and this process can be repeated until the tear has been adequately closed.

Because of the configuration of the suturing devices 10, 310, 410, the physician is able to repair tears in the dural sac and avoid the many nerves that are located within the dural sac. The suturing devices 10, 310, 410 have a desirable J-hook configuration that allows the physician to grasp the target tissue 24 just underneath the internal side 26, and the shape of the distal-most tip 142 allows the physician to indent the target tissue 24 prior to actuation to provide a visual indication of where the needle 20 or 20a will pass through the target tissue. Because of the J-hook configuration of the suturing devices 10, 310, 410, when the physician is positioning the distal-most tip 142 under the internal side 26 of the target tissue 24, the elongate body 14, 314 or 414, 414a can be maintained in an orientation closer to vertical as compared to horizontal. For example with reference to FIGS. 9 and 15, at least the distal end portion 322 of the elongate body 314 can be maintained in an orientation closer to parallel with a central axis CA of the tubular retractor TR as compared to perpendicular with the central axis CA while positioning the distal-most tip 142. This is particularly useful because during spinal surgery the patient is typically lying on his stomach and the physician is working from above the patient. Because of the J-hook configuration of the suturing devices 10 and 410, when the physician is advancing the needle 20 or 20a through the target tissue 24, the needle 20 or 20a is advanced toward the physician, which allows the physician to see the needle. When using either of the suturing devices 10 and 410, at least a portion of the suture 22 remains outside of the patient. Since only a small portion of the suture 22 is received inside the suturing devices 10 or 410, the suturing devices 10 or 410 can be made much smaller as compared to other known suturing device, which makes the suturing devices 10, 410 very useful for repairing tears in a dural sac.

Even though the method of operating the suturing devices was described as passing the needle 20 from inside the dural sac to the outside, the suturing devices 10, 310 and 410 can be used to pass the needle 20 through tissue in other manners, e.g., from outside to inside. Also, the suturing devices 10, 310 and 410 can also be used to suture tissue other than the dural sac.

A method of assembling a suturing device will be described with reference to the suturing device 10 described above; however, the method may be practiced using differently configured suturing devices and/or the variations shown in FIGS. 12-17. The method includes inserting the needle 20 having the suture 22 attached thereto through the distal opening 146 into the needle passage 144 of the needle holder 16 connected with or configured to be connected with the elongate body 14 of the suturing device 10. When assembling the suturing device, the needle 20 is inserted into the needle passage 144 in an insertion direction, which is opposite to the advance direction 36 (see FIG. 3). The method also includes frictionally engaging the inner surface 162 of the needle holder 16 with the needle 20 to retain the first (pointed) end 30 of the needle 20 offset inwardly from the distal opening 146 or offset below the distal-most tip 142 of the suturing device 10. Inserting the needle 20 can further include inserting the second end 32 of the needle 20 and folding the suture 22 such that a portion of the suture 22 extends along the needle passage 144 between the needle 20 and the inner surface 162 (see FIG. 3). The method can further include placing the needle holder 16 with the needle 20 inserted therein and the suture 22 extending out of the distal opening 146 in a package (a sealed package 460 is schematically depicted in FIG. 17), and sealing the package. The method can further include removing the needle holder 16 from a sealed package prior to inserting the needle 20 into the needle passage 144. Accordingly, the needle 20 can be inserted into the needle passage 144 in the operating room or surgical facility instead of at the manufacturing facility, if desired. Frictionally engaging the inner surface 162 of the needle holder 16 can further include contacting the inner surface 162 of the needle holder 16 in at least three different locations along the needle 20 when the needle 20 is in a retracted position (see FIGS. 3 and 16). When in the retracted position, the needle 20 can contact the inner surface 162 of the needle holder 16 at the first location 164, the second location 166 and the third location 168 shown in FIG. 16.

The method of assembling the suturing device 10 can also include inserting the needle 20 having the suture 22 attached thereto through the distal opening 146 into the needle passage 144 of a suturing device 10. The method also includes maintaining a portion of the suture 22 extending out of the distal opening 146 and outside of the suturing device 10. As mentioned above, inserting the needle 20 can further include inserting the second end 32 of the needle 20 and folding the suture 22 such that a portion of the suture 22 extends along the needle passage 144 between the needle 20 and the inner surface 162 (see FIG. 3). FIG. 12 shows the variant including the keyway 220. The method can further include inserting the suture 22 into the keyway 220 while inserting the needle 20 through the distal opening 146 into the needle passage 144 of the suturing device 10. Inserting the needle 20 having the suture 22 attached thereto can further include pushing the needle 20 into the needle passage 144 until the needle 20 frictionally engages the inner surface 162 of the suturing device 10 defining the needle passage 144. Inserting the needle 20 having the suture 22 attached thereto can also include inserting the second end 32 of the needle 20 and folding the suture 22 such that a portion of the suture 22 extends along the needle passage 144 between the needle 20 and the inner surface 162 (see FIG. 3) of the suturing device 10 defining the needle passage 144.

It will be appreciated that various of the above-disclosed embodiments and variations and other features and functions, or alternatives or varieties thereof, may be desirably combined into many other different devices or applications. Also, components from one embodiment can be used in other embodiments described above. Also, various presently unforeseen or unanticipated alternatives, modifications, variations or improvements therein may be subsequently made by those skilled in the art which are also intended to be encompassed by the following claims.

The invention claimed is:

1. A suturing device comprising:
    an elongate body including a proximal end portion and a distal end portion;
    an actuator interacting with the elongate body and operable between a first operating position and a second operating position;
    a needle holder extending away from the distal end portion or provided as part of the distal end portion of the elongate body, the needle holder including a distal end section having a distal-most tip, the needle holder defining a needle passage and a distal opening adjacent the distal-most tip; and
    a knot pusher connected with and extending away from at least one of the elongate body and the needle holder, wherein the knot pusher includes a lower concave surface.

2. The suturing device of claim 1, wherein at least one of the knot pusher and the needle holder is releasably connected with the elongate body.

3. The suturing device of claim 1, wherein the lower concave surface includes an inflection offset from a longitudinal axis of the elongate body in the same direction that the distal-most tip is offset from the longitudinal axis.

4. The suturing device of claim 1, wherein the needle holder is a curved needle holder and the knot pusher extends from an outer surface of the curved needle holder, and the outer surface of the curved needle holder is curved.

5. The suturing device of claim 4, wherein the needle passage follows a curved needle passage radius, wherein the outer surface of the curved needle holder extends along a radius that is equal in magnitude to the curved needle passage radius of the needle passage.

6. A suturing device comprising:
    an elongate body including a proximal end portion and a distal end portion;
    an actuator interacting with the elongate body and operable between a first operating position and a second operating position;
    a needle holder extending away from the distal end portion or provided as part of the distal end portion of the elongate body, the needle holder including a distal end section having a distal-most tip, the needle holder defining a needle passage and a distal opening adjacent the distal-most tip, and
    a knot pusher connected with and extending away from at least one of the elongate body and the needle holder, wherein the knot pusher includes an external side surface extending along a plane parallel to and offset from a longitudinal axis of the elongate body, wherein the needle passage follows a curved needle passage radius, which resides in a first plane, wherein a second plane is perpendicular to the first plane, parallel to the longitudinal axis, intersected by a line along an outer surface of the elongate body further from the distal-most tip, wherein no portion of the knot pusher extends in a direction away from the distal-most tip beyond the second plane.

7. The suturing device of claim 6, wherein the elongate body has a bayonet configuration, and the external side surface extends along the plane parallel to and offset from a longitudinal axis of the distal end portion of the elongate body.

8. The suturing device of claim 6, wherein at least one of the knot pusher and the needle holder is releasably connected with the elongate body.

9. A suturing device comprising:
    an elongate body including a proximal end portion and a distal end portion;
    an actuator interacting with the elongate body and operable between a first operating position and a second operating position;
    a needle holder extending away from the distal end portion or provided as part of the distal end portion of the elongate body, the needle holder including a distal end section having a distal-most tip, the needle holder defining a needle passage and a distal opening adjacent the distal-most tip; and a knot pusher connected with and extending away from at least one of the elongate body and the needle holder, wherein the knot pusher includes an external side surface and a maximum distance measured perpendicular to a longitudinal axis of the elongate body between the external side surface and the distal-most tip is less than 10 mm.

10. The suturing device of claim 9, wherein the knot pusher is releasably connected with the elongate body.

11. The suturing device of claim 10, wherein the needle holder is releasably connected with the elongate body.

12. The suturing device of claim 9, wherein the needle holder is releasably connected with the elongate body.

13. The suturing device of claim 12, wherein the knot pusher is releasably connected with the elongate body.

14. A suturing device comprising:

an elongate body including a proximal end portion and a distal end portion;

an actuator interacting with the elongate body and operable between a first operating position and a second operating position;

a needle holder extending away from the distal end portion or provided as part of the distal end portion of the elongate body, the needle holder including a distal end section having a distal-most tip, the needle holder defining a needle passage and a distal opening adjacent the distal-most tip;

a knot pusher connected with and extending away from at least one of the elongate body and the needle holder a curved needle having first end, which is pointed, and a second end, wherein the curved needle is received in the needle passage; and a suture connected with the curved needle.

15. The suturing device of claim 14, wherein at least a portion of the suture extends through the distal opening when the curved needle is received in the needle passage and the actuator is in the first operating position.

16. The suturing device of claim 15, wherein at least a portion of the suture extends along the needle passage toward the distal opening between the curved needle and an inner surface of the needle holder when the curved needle is received in the needle passage and the actuator is in the first operating position.

17. A suturing device comprising:

an elongate body including a proximal end portion and a distal end portion;

an actuator interacting with the elongate body and operable between a first operating position and a second operating position;

a needle holder extending away from the distal end portion or provided as part of the distal end portion of the elongate body, the needle holder including a distal end section having a distal-most tip, the needle holder defining a needle passage and a distal opening adjacent the distal-most tip; and a knot pusher connected with and extending away from at least one of the elongate body and the needle holder wherein a distal extent of the suturing device is at a point along the needle holder, which is curved, where a tangent line is perpendicular to a longitudinal axis of the elongate body.

18. The suturing device of claim 17, wherein the elongate body has a bayonet configuration.

* * * * *